(12) United States Patent
Leuthardt et al.

(10) Patent No.: US 7,120,486 B2
(45) Date of Patent: Oct. 10, 2006

(54) BRAIN COMPUTER INTERFACE

(75) Inventors: Eric C. Leuthardt, St. Louis, MO (US); Gerwin Schalk, Albany, NY (US); Daniel W. Moran, Ballwin, MO (US); Jonathan Rickel Wolpaw, Delmar, NY (US); Jeffrey G. Ojemann, Seattle, WA (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 10/735,474

(22) Filed: Dec. 12, 2003

(65) Prior Publication Data

US 2005/0131311 A1 Jun. 16, 2005

(51) Int. Cl.
    *A61B 5/04* (2006.01)
(52) U.S. Cl. ...................... 600/545; 600/544
(58) Field of Classification Search ........ 600/544–546; 623/25; 345/158, 160, 163
    See application file for complete search history.

(56) References Cited

U.S. PATENT DOCUMENTS

| 4,735,208 | A |   | 4/1988  | Wyler et al.         |         |
|-----------|---|---|---------|----------------------|---------|
| 4,987,411 | A | * | 1/1991  | Ishigami             | 345/159 |
| 5,298,890 | A | * | 3/1994  | Kanamaru et al.      | 345/157 |
| 5,638,826 | A | * | 6/1997  | Wolpaw et al.        | 600/544 |
| 6,091,979 | A |   | 7/2000  | Madsen               |         |
| 6,143,440 | A |   | 11/2000 | Volz et al.          |         |
| 6,171,239 | B1| * | 1/2001  | Humphrey             | 600/372 |
| 6,304,775 | B1|   | 10/2001 | Iasemidis            |         |
| 6,349,231 | B1|   | 2/2002  | Musha                |         |
| 6,591,138 | B1|   | 7/2003  | Fischell             |         |
| 6,597,954 | B1|   | 7/2003  | Pless et al.         |         |
| 6,609,017 | B1| * | 8/2003  | Shenoy et al.        | 600/372 |
| 6,615,076 | B1| * | 9/2003  | Mitra et al.         | 600/544 |
| 6,647,296 | B1|   | 11/2003 | Fischell et al.      |         |
| 2004/0082875 | A1 |  | 4/2004 | Donoghue et al.     |         |
| 2004/0138570 | A1 |  | 7/2004 | Nita et al.         |         |
| 2005/0113744 | A1 | * | 5/2005 | Donoghue et al.     | 604/66  |

OTHER PUBLICATIONS

Laconte et al., "Designing a Subdural Electrocorticography Telemitter for Human Patients with Epilepsy," Apr., 2003, 34 pages.
Laubach et al., "Cortical Ensemble Activity Increasingly Predicts Behaviour Outcomes During Learning of a Motor Task," Nature, 2000, pp. 567-571, vol. 405.
Lee et al., "Synchronous Gamma Activity: A Review and Contribution to an Integrative Neuroscience Model of Schizophrenia," Brain Research Reviews, 2003, pp. 57-78, vol. 41.
Leuthardt et al., "A Brain-Computer Interface Using Electrocorticographic Signals in Humans," J. Neural Eng., 2004, pp. 63-71, vol. 1.
Pfurtscheller et al., "Early Onset of Post-Movement Beta Electroencephalogram Synchronization in the Supplementary Motor Area During Self-Paced Finger Movement in Man," Neuroscience Letters, 2003, pp. 111-114, vol. 339.
Srinivasan, "Methods to Improve the Spatial Resolution of EEG," IJBEM, 1999, pp. 102-111, vol. 1.

(Continued)

*Primary Examiner*—Robert L. Nasser
*Assistant Examiner*—Patricia C Mallari
(74) *Attorney, Agent, or Firm*—Sonnenschein Nath & Rosenthal LLP

(57) ABSTRACT

An electrocorticography-based brain computer interface (BCI) and related methods are described.

13 Claims, 13 Drawing Sheets

Condition 1. Imagine Saying Move, directs cursor upwards
Condition 2. Rest, directs cursor downward

OTHER PUBLICATIONS

Wolpaw et al., "Brain-Computer Interfaces for Communication and Control," Clinical Neurophysiology, 2002, pp. 77-791, vol. 113.

Babiloni et al., "Linear Classification of Low-Resolution EEG Patterns Produced by Imagined Hand Movements," IEEE Trans. Rehabil. Eng., 2000, pp. 186-187, vol. 8.

Barinaga, "Remaping the Motor Cortex," Science, 1995, pp. 1696-1698, vol. 268.

Bayliss et al., A Virtual Reality Testbed for Brain-Computer Interface Research, IEEE Trans. Rehabil. Eng., 2000, pp. 188-189, vol. 8.

Birbaumer et al., The Thought Translation Device (TTD) for Completely Paralized Patients, IEEE Trans. Rehabil. Eng., 2000, pp. 190-197, vol. 8.

Birch et al., "Brain-Computer Interface Research at the Neil Squire Foundation," IEEE Trans. Rehabil. Eng., 2000, pp. 193-197, vol. 8.

Crone et al., Induced Electrocorticographic Gamma Activity During Auditory Perception, Clin. Neurophysiol., 2001, 112: 565-582, vol. 112.

Curran et al., "Learning to Control Brain Activity: A Review of the Production and Control of EEG Components for Driving Brain-Computer Interface (BCI) Systems," Brain and Cognition, 2003, pp. 326-336, vol. 51.

Donchin et al., "The Mental Prosthesis: Assessing the Speed of a P300-Based Brain-Computer Interface," IEEE Trans. Rehabil. Eng., 2000, pp. 174-179, vol. 8.

Freeman et al., "Spatial Spectra of Scalp EEG and EMG from Awake Humans," Clinical Neurophysiology, 2003, pp. 1-16.

Graffin et al., "EEG Concomitants of Hypnosis and Hypnotic Susceptibility," J. Abnormal Physho., 1995, pp. 123-131, vol. 104.

Graimann et al., "Visualization of Significant ERD/ERS Patterns in Multichannel EEG and ECoG Data," Clin. Neurophys., 2002, pp. 43-47, vol. 113.

Isaacs et al., "Work Toward Real-Time Control of a Cortical Neural Prothesis," IEEE Trans. Rehabil. Eng., 2000, pp. 196-213, vol. 8.

Kennedy et al., "Direct Control of a Computer from the Human Central Nervous System," IEEE Trans. Rehabil. Eng., 2000, pp. 198-202, vol. 8.

Kennedy et al., Restoration of Neural Output from a Paralyzed Patient by a Direct Brain Connection, Neuroreport, 1998, pp. 1707-1711, vol. 9.

Kostov et al., "Parallel Man-Machine Training in Development of EEG-Based Cursor Control," IEEE Trans. Rehabil. Eng., 2000, pp. 203-205, vol. 8.

Lauer et al., "Applications of Cortical Signals to Neuroprosthetic Control: A Critical Review," IEEE Trans. Rehabil. Eng., 2000, pp. 205-207, vol. 8.

Lee et al., "Cortical Potentials Related to Voluntary and Passive Finger Movements Recorded from Subdural Electrodes in Humans," Ann. Neurol., 1986, pp. 32-37, vol. 20.

Levine et al., "A Direct Brain Interface Based on Event-Related Potentials," IEEE Trans. Rehabil. Eng., 2000, pp. 180-185, vol. 8.

Levine et al., "Preliminary Work on a Direct Brain Interface for Control of Assistive Technologies," downloaded from http://www.engin.umich.edu/dbi/nih2000/concept.html.

Makeig et al., "A Natural Basis for Efficient Brain-Actuated Control," IEEE Trans. Rehabil. Eng., 2000, pp. 208-210, vol. 8.

Middendorf et al. "Brain-Computer Interfaces Based on the Steady-State Visual-Evoked Response," IEEE Trans. Ehabil. Eng., 2000, pp. 211-214, vol. 8.

Miner et al., "Answering Questions with an Electroencephalogram-Based Brain-Computer Interface," Arch. Phys. Med. Rehabil., 1998, pp. 1029-1033, vol. 79.

Onofrj et al., "Even Related Potentials Recorded in Patients with Locked-In Syndrome," J. Neurol. Neurosurg., 1997 (6 pages).

Perelmouter et al., "A Binary Spelling Interface with Random Errors," IEEE Trans. Rehabil. Eng., 2000, pp. 227-232, vol. 8.

Pfurtscheller, et al., Frequency Dependence of the Transmission of the EEG from Cortex to Scalp, Electroencephalogr. Clin. Neurophysiol., 1975, pp. 93-96, vol. 38.

Pfurtscheller et al., Spatiotemporal Patterns of Beta Desynchronization and Gamma Synchronization in Corticographic Data During Self-Paced Movement, Clin. Neurophysiol., 2003, pp. 1226-1236, vol. 114.

Pfurtscheller et al., Event-Related EEG/MEG Synchronization and Desynchronization: Basic Principles, Clin. Neurophysiol., 1999, pp. 1842-1857, vol. 110.

Pfurtscheller et al., Current Trends in Graz Brain-Computer Interface (BCI) Research, IEEE Trans. Rehabil. Eng., 2000, pp. 216-219, vol. 8.

Schalk et al., "BCI2000: A General Purpose Brain Computer Interface (BCI) System for Research and Development," IEEE Trans. Biomed. Eng., 2003, pp. 1-10, vol. 10.

Serruya et al., "Instant Neural Control of a Movement Signal," Nature, 2002, pp. 141-142, vol. 416.

Taylor et al., "Direct Cortical Control of 3D Neuroprosthetic Devices," Science, 2002, pp. 1829-1832, vol. 296.

Wessberg et al., "Real-Time Prediction of Hand Trajectory by Ensembles of Cortical Neurons in Primates," Nature, 2000, pp. 361-365, vol. 408.

Wolpaw et al., "Brain-Computer Interface Research at the Wadsworth Center," IEEE Trans. Rehabil. Eng., 2000, pp. 222-226, vol. 8.

Wolpaw et al., "Brain-Computer Interface Technology: A Review of the First International Meeting," IEEE Trans. Rehabil. Eng., 2000, pp. 164-173, vol. 8.

\* cited by examiner

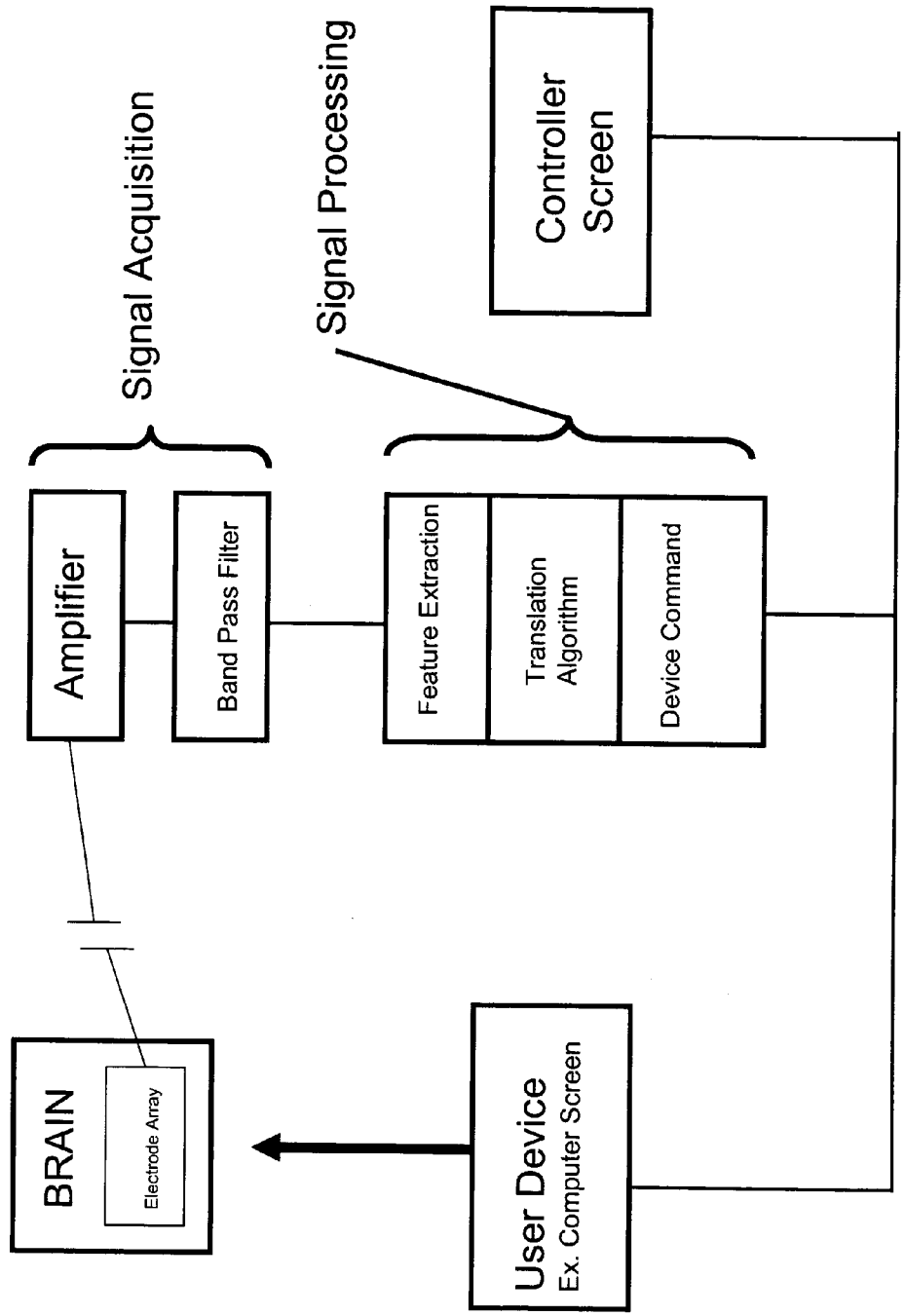

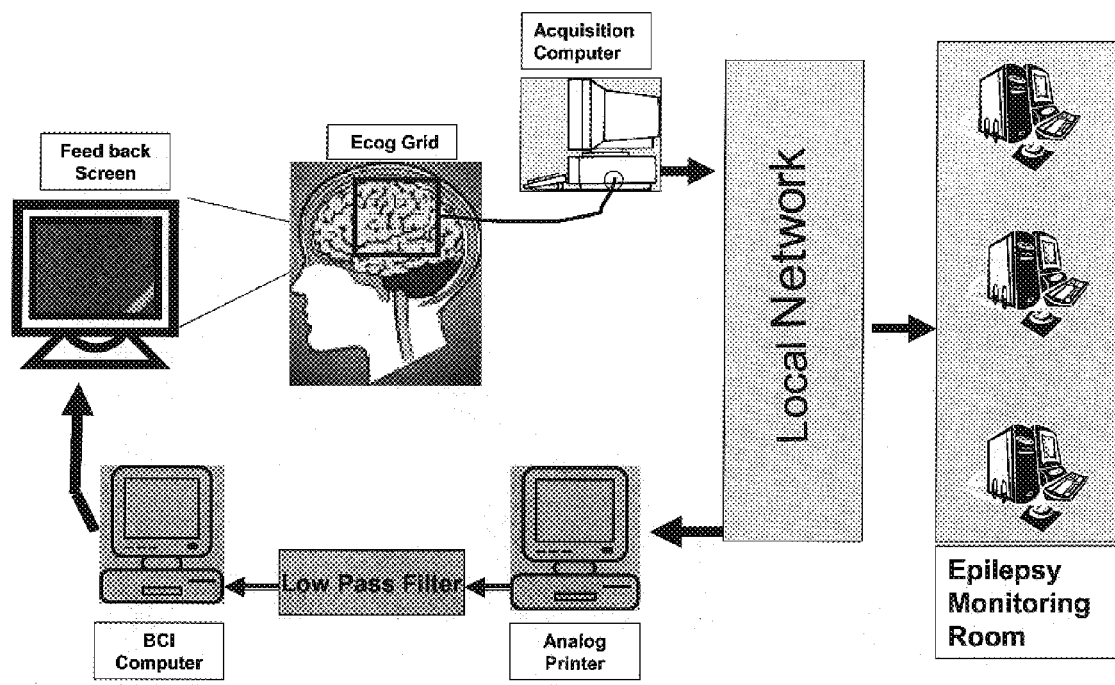
Figure 3a. Ecog BCI - System

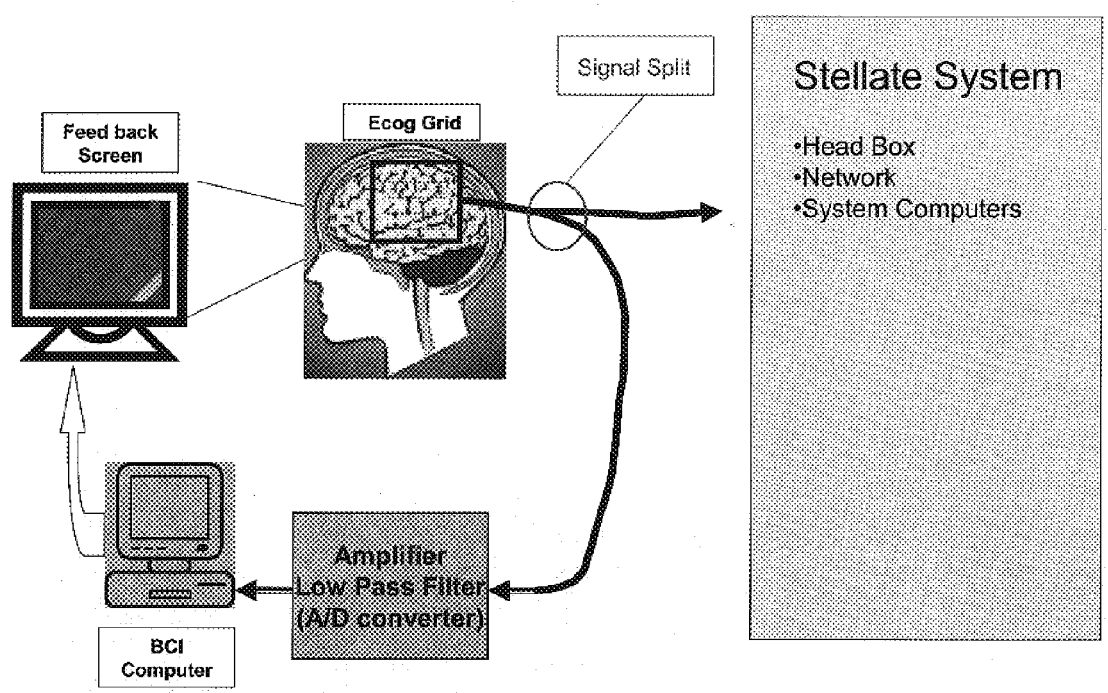

Condition 1. Imagine Saying Move, directs cursor upwards
Condition 2. Rest, directs cursor downward Middle Finger         Thumb

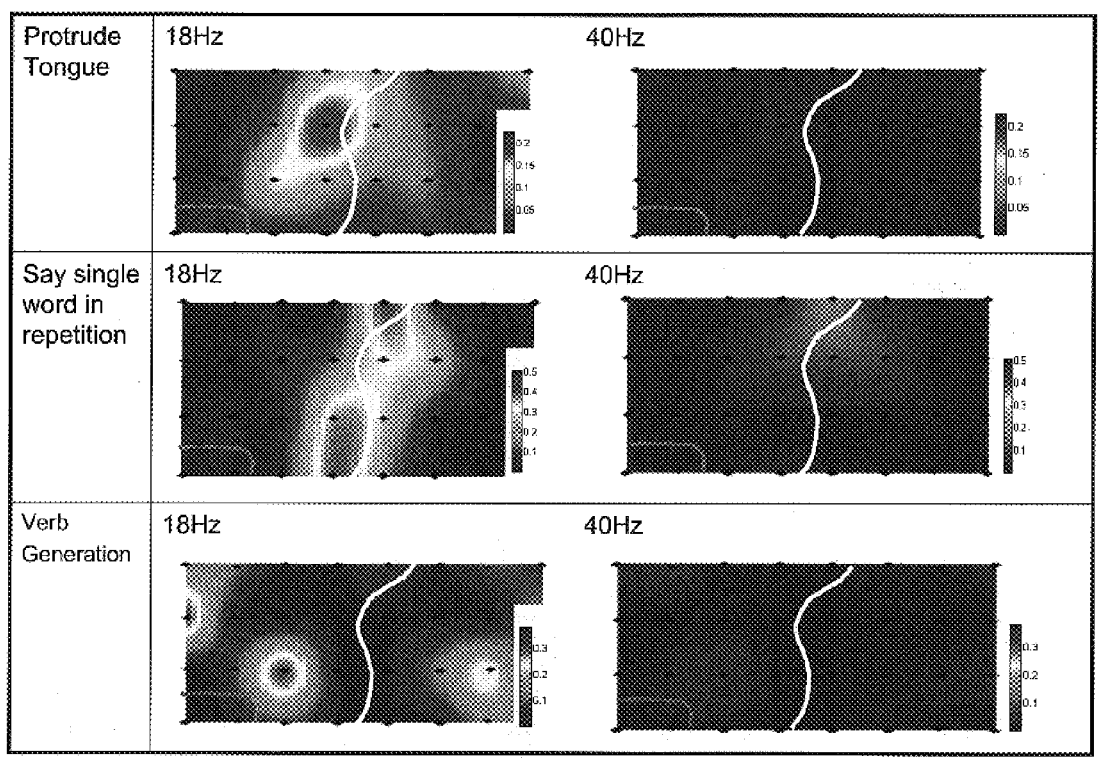
Figure 12: Analysis of Motor Speech

BRAIN COMPUTER INTERFACE

STATEMENT REGARDING FEDERALLY SPONSORED RESEARCH OR DEVELOPMENT

This invention is based in part on research performed with U.S. government grant support under grant numbers NS41272, HD30146 and EB00856 from the National Institutes of Health. The U.S. government has certain rights in the invention.

RELATED APPLICATIONS

Not applicable.

REFERENCE TO A SEQUENCE LISTING

Not applicable.

BACKGROUND OF THE INVENTION

1. Field of the Invention

This invention relates in general to the fields of bioengineering and computer technology, and more particularly to a novel brain-computer interface and related methods involving generating electrical outputs from raw brain signals.

2. Description of the Related Art

Brain-computer interfaces (BCI) are systems that provide communications between human beings and machines. BCI's can be used, for example, by individuals to control an external device such as a wheelchair. A major goal of brain-computer interfaces (BCI) is to decode intent from the brain activity of an individual, and signals representing the decoded intent are then used in various ways to communicate with an external device. BCI's hold particular promise for aiding people with severe motor impairments.

Several signal acquisition modalities are currently used for BCI operation in human and non-human primates. These include electroencephalographic signals (EEG) acquired from scalp electrodes, and single neuron activity assessed by microelectrodes arrays or glass cone electrodes. EEG is considered a safe and non-invasive modality, but has low spatial resolution and a poor signal to noise ratio due to signal attenuation by the skull, and signal contamination from muscle activity. In contrast, single-unit recordings of the signals from an individual neuron convey a significantly finer spatial resolution with higher information transfer rates and enable the use of more independent channels. However, single unit recordings require close proximity (within 100 microns) with neurons and therefore are not generally suitable for human applications because of the much higher associated clinical risk, and the lack of durable effect secondary to scar formation around the electrodes.

BCI systems that have achieved closed loop, continuous, and real time control in human subjects are known and typically utilize EEG signal. Most closed loop trials using such systems have utilized low frequency band power changes associated with sensorimotor cortex, known as the mu and beta rhythms. The mu and beta rhythms are thought to be the product of thalamocortical circuits that show suppressed frequency power on cortical activation. These power suppressions, also known as Event Related Descynchronizations (ERD), can be induced by both actual and imagined motor movements. The mu rhythms (8–12 Hz) and beta rhythms (18–26 Hz) are separable in regards to timing and topographical distribution, but tend to show diffuse bilateral (contralateral dominant) suppression with a given motor activity. Additionally, more regionally specific higher frequency bands, known as gamma rhythms, have also been investigated. The gamma band (>30 Hz) is often associated with an increased power (Event Related Synchronization—ERS) in association with cortical activation and has been postulated to be associated with motor programming, attention, and sensorimotor integration. These higher frequency oscillations have not been utilized in a BCI system.

U.S. Pat. No. 5,638,826 (Wolpaw) describes a BCI system using electroencephalographic signal (EEG) in which mu rhythm suppressions (8–12 Hz) are utilized.

U.S. Pat. No. 6,349,231 describes a hybrid BCI based on EEG brain waves in combination with the biopotentials produced by muscles, heart rate, eye movements, and eye blinks.

However, known BCI systems remain limited by the constraints on spatial resolution and signal strength imposed by the chosen signaling modality, such as the constraints imposed by using EEG. Therefore, a need remains for improved BCI systems that are more readily adaptable to human clinical applications.

BRIEF DESCRIPTION OF THE DRAWINGS

FIG. 2 is a schematic diagram of signal processing in an ECoG-based BCI;

FIG. 3a is a block diagram of a first exemplary embodiment of an ECoG-based BCI;

FIG. 3b is a block diagram of a second exemplary embodiment of an ECoG-based BCI;

FIG. 12 is a table of topograms from one subject showing regional frequency changes at 18 Hz (left column), and 40 Hz (right column) with a given task including tongue protrusion, repetitive speech, and verb generation.

DETAILED DESCRIPTION OF THE INVENTION

Figure 1:
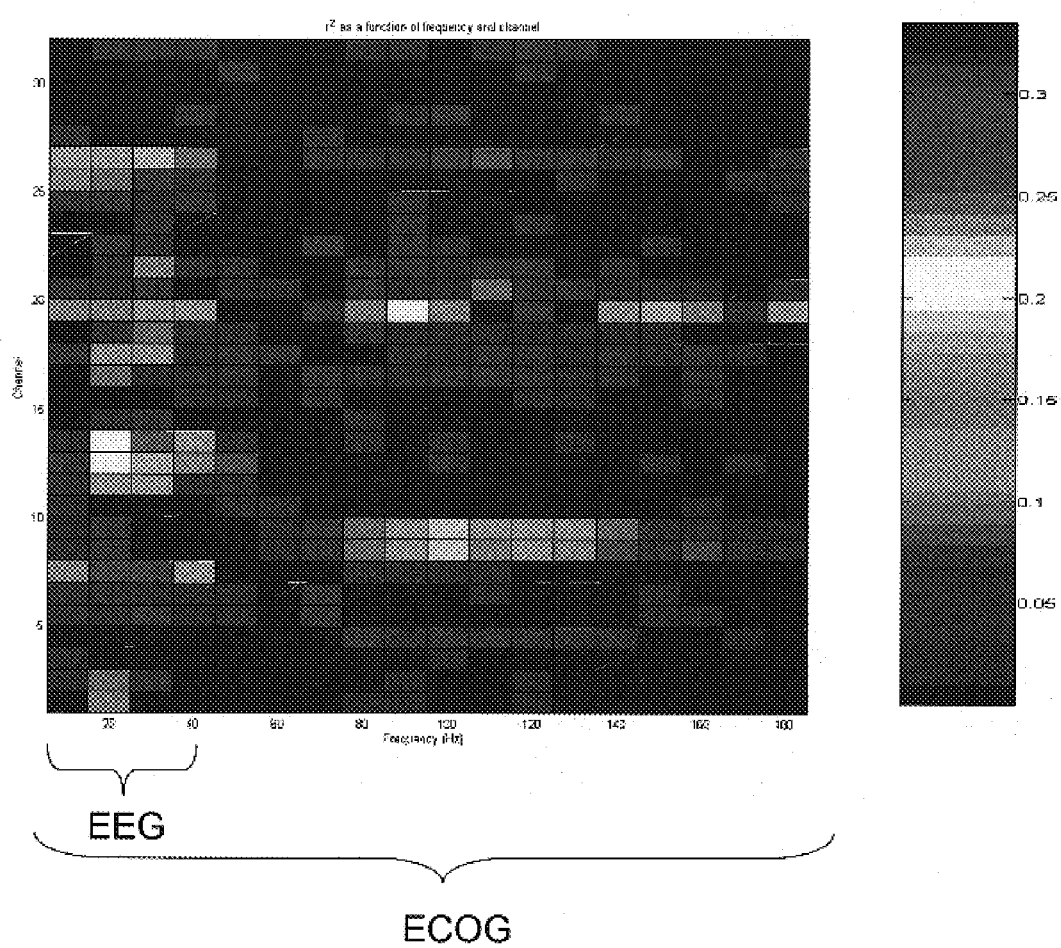
FIG. 1 is an analysis of variance of frequency changes for a given active task condition (in the example, imagining saying the word "move") versus an inactive rest condition.

The features, aspects and advantages of the present invention will become better understood with reference to the following description, examples and appended claims.

Definitions

To facilitate understanding of the invention, certain terms as used herein are defined below as follows:

As used interchangeably herein, the terms "ECoG" and "electrocorticography" refer to the technique of recording the electrical activity of the cerebral cortex by means of electrodes placed directly on it, either under the dura mater (subdural) or over the dura mater (epidural) but beneath the skull.

As used interchangeably herein, the terms "BCI" and "brain computer interface" refer to a signal-processing circuit that takes input in the form of raw brain signals and converts the raw signals to a processed signal that can be input to a digital device for storage and further analysis.

As used herein, the term "BCI system" refers to an organized scheme of multiple components including a BCI as defined above, that together serve the function of translating raw brain signals to an output of a device, where the raw signals are derived from the central nervous system of a user of the system.

As used herein, the term "device" refers to a piece of equipment or a mechanism designed to serve a special purpose or function. In the examples, the device is a cursor on a video monitor. Other examples of devices within the intended meaning of the term include, without limitation, wheelchairs and prosthestics. The term also embraces mechanisms that can be used to control other mechanisms, such as steering wheels, joysticks, levers, buttons and the like.

The invention is based in part on the discovery that ECoG signals can be successfully used in a BCI to control an external device in real time, and further in part on the surprising finding that ECoG signals can provide information required for control in at least two-dimensions. Prior to the present invention, the use of ECoG signals in a BCI had not been demonstrated.

Until about twenty years ago, the overwhelmingly dominant paradigm for investigating the physiologic and anatomic bases of cognitive function in humans was based on analysis of brain lesions. More recently, techniques such as functional magnetic resonance imaging (fMRI), positron emission tomography (PET), single photon emission computerized tomography (SPECT), and electrophysiological analyses such as electroencephalography (EEG), magnetoencephalography (MEG), and electrocorticography (ECoG) have become available. While these technologies have allowed researchers to go beyond the traditional approach of lesional analyses, each retains some limitations.

Functional neuroimaging has been defined as the "process of assigning a physiologic parameter indexing some aspect of brain function to a spatial representation of the brain." (Graboski and Damasio, 2000). The dominant technologies of this sort are fMRI using blood oxygenation level dependent (BOLD) contrast and PET using [$^{15}$O]H$_2$O tracer. These technologies assess changes in physiologic processes such as blood flow, blood oxygenation, and glucose metabolism, which are believed to be coupled to local synaptic activity. (Villringer and Dirnagl, (1995); Jueptner and Weiller (1995)). As a result, both techniques have provided new opportunities for spatially delineating regions associated with various aspects of human cognitive function. However, the spatial and temporal resolution of these methods is relatively coarse due to a reliance on metabolic and hemodynamic response. The optimal resolution of fMRI is approximately 1–5 mm spatially and 1–2 seconds temporally, and for PET is about 1 cm spatially and 10 seconds temporally. Additionally, the precise relationship between underlying neuronal events and the metabolic and hemodynamic responses subserving fMRI and PET is not well understood. Accordingly, fMRI and PET data can be difficult to interpret, as demonstrated by the assessment of functional measures in the context of synaptic inhibition and the interpretation of decreased blood flow or metabolism for a given cognitive activity.

Another approach to investigating brain function involves the use of electrical signals of brain activity, which provides the basis for methods such as EEG, MEG, and ECoG. Such techniques are complementary to the more anatomic approaches of PET and fMRI, allowing for improved temporal resolution and a more direct assessment of the electrophysiologic dynamics associated with various brain induced events.

EEG, MEG and ECoG provide signals with features that are associated with cortically related events. Such features include time-locked neuronal changes induced by sensory stimuli known as event related potentials (ERPs), or ongoing non-phase-locked fluctuations associated with frequency power changes. ERPs are thought to be a series of transient post synaptic responses of main pyramidal neurons triggered by a specific stimulus. The frequency power changes are hypothesized to be due to an increase or decrease in the synchrony of the intrinsic oscillations of the underlying neuronal populations.

Certain frequency bands have been identified with certain types of cortical activation. Alpha rhythms (over visual cortex) and mu rhythms (over somatosensory cortex) are 8–12 Hz and are thought to be the product of thalamocortical circuits which show suppressed frequency power on cortical activation. These power suppressions are also known as Event Related Descynchronizations (ERD). The mu rhythms can also often associated with beta rhythms (18–26 Hz) but are separable in regards to timing and topographical distribution. More regionally specific higher frequency bands, known as gamma rhythms (>30 Hz), have also been investigated. The gamma band is often associated with an increased power (Event Related Synchronization—ERS) in association with cortical activation and has been postulated to be associated with motor programming, attention, and sensorimotor/multimodal sensory integration.

EEG has been the most commonly used technique for acquiring these electrical signals of brain activity because EEG is non-invasive and therefore low risk, is relatively low-cost, and is widely applicable. However, due to signal attenuation by the skull and electrical noise contamination from muscle activity, the signal-to-noise ratio of EEG is low and the spatial and frequency resolution is poor. The maximal spatial discrimination with EEG is approximately 3 centimeters and the appreciable frequency range is 0–40 Hz.

Magnetoencephalography is also a non-invasive modality with a similar profile as that of EEG, but has an improved spatial resolution of approximately 4 to 10 millimeters. In contrast, ECoG requires a craniotomy for electrode placement. Though invasive, the ECoG platform provides a combination of high spatial resolution on the order of 1–2 mm with a broader frequency range of approximately 0–200 Hz.

Conventional (i.e., EEG-based) BCI systems use very specific brain signals in limited frequency ranges below 40 Hz. Examples of such signals include the mu/beta rhythms (around 10/20 Hz, respectively), slow cortical potentials, and P300 evoked potentials. In contrast, since ECoG signals have a much higher frequency range, and higher spatial resolution, ECoG signals exhibit different signal characteristics. Accordingly, electrode locations or frequencies that are used in conventional EEG-based systems are not helpful in ECoG-based systems. Until now, the electrode configurations, frequencies and signal characteristics useful in ECoG-based systems though investigated have never been used and defined for online control. The present ECoG-based BCI system uses a distinct set of signal characteristics and analyses.

Electrocorticography signals have not yet been used in a BCI system enabling an individual to maintain continuous device control in real time and with continuous feedback using electrocorticographic signals. However, ECoG activity is well-suited for BCI applications. The ECoG signal is recorded from electrodes positioned at the brain surface, with lower clinical risks than intra-cortical electrode devices, while at the same time offering a much more robust signal than EEG, both in terms of spatial and resolution and temporal resolution. The ECoG signal magnitude is typically five to ten times larger (0.05–1.0 mV versus 0.01–0.02 mV for EEG) than EEG, has a much higher spatial resolution as it relates to electrode spacing (0.125 cm versus 3.0 cm for EEG), and has more than four times the frequency bandwidth of EEG (0–200 Hz versus 0–40 Hz for EEG). Thus, ECoG signals represent a smaller population of neurons than does EEG, and discriminate across a broader range of frequencies including frequencies greater than 40 Hz. An ECoG-based BCI not only enables the full use of mu rhythms, but also the use of the much higher frequency bands (beta and gamma) that are thought to be more closely associated with higher specific cortical function.

Signal analysis of brain signals generated by ECoG demonstrates how ECoG signals compare very favorably to EEG signals. FIG. 1 shows an example of a standard spectral analysis of variance of frequency changes for a human subject during a given active condition (for example, imagining saying the word "move") versus the rest, inactive condition. The channels are the ordinate (y) axis and the frequency is the abscissa (x) axis. The ranges appreciable by EEG and ECoG are shown. The data gathered from each of the 32 electrodes with each of the tasks was used to identify the frequency bands in which amplitude was different between the task and rest. FIG. 1 illustrates these analyses for a given subject. In this example, the subject's task was to imagine saying the word "move." FIG. 1 demonstrates that the range of reactive frequencies extends well beyond 40–50 Hz, which is the maximum value reported for EEG-based systems. Moreover, unlike EEG signals, the signal-to-noise ratio of the ECoG signal is improved by the skull rather than attenuated, and ECoG signals are not contaminated by muscle electrical activity.

In addition, the subdural electrodes from which the ECoG signal is derived do not need to penetrate cortex as is required with microelectrode systems. Therefore, scarring and subsequent encapsulation of the recording sites is less of a factor with ECoG electrodes than with intra-cortical microelectrodes. It is expected that these characteristics will translate to increased implant viability over time, which is an important consideration for clinical applications.

Accordingly, the present invention uses ECoG signals in a BCI system and related methods, and is based in part based on the surprising discovery that ECoG-based BCI provides novel and unexpected advantages over BCI's using EEG or other signal acquisition platforms. The ECoG-based system unexpectedly requires much less time than required with EEG-based BCI systems for a user to learn to gain control and improve performance. ECoG signal control is achieved following a single training session of an hour or less, and learning can occur over minutes. In contrast, control of EEG signal takes much longer to achieve and learning occurs over a time course of days to weeks. In addition, the higher spatial and signal resolution of ECoG relative to EEG allows for two or more degrees of freedom of control. With ECoG signals, the information for two-dimensional discrimination is present with a very coarsely spaced electrode array. Additionally, individual finger movements can be distinguished with ECoG, which has never been seen with EEG. The likelihood that more degrees of freedom can be achieved with a higher density electrode array is very high. Moreover, unlike EEG, the ECoG-based system utilizes non-sensorimotor signals and tasks. For example, the ECoG-based system enables the use of speech tasks that drive brain signaling in speech cortex, including Broca's speech center, and premotor cortex. An individual thinking about the word "move" generates signals in speech cortex that are accessible to ECoG, which are then used to gain overt control over an external device.

FIG. 2 is a schematic diagram of the signal processing in an ECoG-based BCI. An exemplary ECoG-based BCI system and related methods use ECoG signal from the brain and translate that activity into the intent of the user. ECoG signal can be acquired using an electrode array that is either under the dura mater (subdural) or over the dura mater (epidural), although in an exemplary embodiment the electrode array is subdural. The signal is routed to the acquisition computer either directly through lead wires or indirectly through a wirelessly transmitted signal. A computer is further configured to analyze the ECoG signal to determine the intent of the user. The intent of the user is then communicated to a device, such as a screen cursor, or a wheelchair or prosthetic device to control the device accordingly. The BCI configuration enables this control continuously and in real time, using closed loop feedback to the user.

In an exemplary embodiment, signal acquisition hardware is typically a subdural electrode array, which is implanted beneath the dura mater of the user and generates the raw ECoG signal. The signal is passed through an amplifier and a band pass filter. The signal is then provided as an input to a computer running software configured to extract features of the signal, apply a translation algorithm to the signal features as they vary under varying behavioral conditions of the user, and then generate a device command derived from the processed, translated signal. In one embodiment, the device command is communicated to a user screen on a computer monitor, and controls the position of a cursor on the screen. For training of the user on the ECoG-based BCI, the position of the cursor provides visual feedback to the user as to the effect of the user's brain signals on the cursor position. The user then uses the feedback information to modify conscious instructions, thereby for improving accuracy of cursor position control. The device command is also communicated to a controller screen, which serves to manifest the intentions of the user. For example, when the user intends for the cursor to go up, the cursor moves up.

FIG. 3a is a block diagram of one embodiment of the ECoG-based BCI in which the ECoG signal is routed through a network prior to being sent to a BCI computer. The user, having an ECoG electrode implant, views the user feedback screen. Raw ECoG signals from the ECoG electrodes are passed to a data acquisition computer configured for collecting and storing the raw ECoG signal. Raw and processed signals from the acquisition computer, and the device command, are communicated via a local area network to a computer or computers configured to provide signals for monitoring, for example in a monitoring room, and to an analog printing device. In an exemplary embodiment, an XLTEK networking (available from XLTEK, Ontario, Canada) or similar system such as that available from Stellate (Montreal, Quebec, Canada) is used for the network and for the analog printer for pulling signals off the local network, and for signal processing on the network. The signal is further passed through a low pass-filter (e.g. from United Electronics Industries, Inc., Canton, Mass.) and to the BCI computer, which is a desktop computer configured for feature extraction, application of the translation algorithm, and generation of a device command. For example, the BCI computer is configured in part for feature extraction by being capable of reading 32 channels in real time, with no more than a 60 msec lag. The device command is communicated to an output device, which in one embodiment is a feedback screen for viewing by the user.

FIG. 3b shows a system that is directly routed to the BCI computer, demonstrating a variation of the process in which the ECoG signal is sent directly to an amplifier, band pass filter, and analog-to-digital converter, (such as, for example, g.USBamp, available from "g tec", Guger Technologies, 8020 Graz, Austria, Europe) and then subsequently sent to a BCI computer running the same programs configured for feature extraction, translational algorithm, and device commands as previously described supra.

Figure 4:
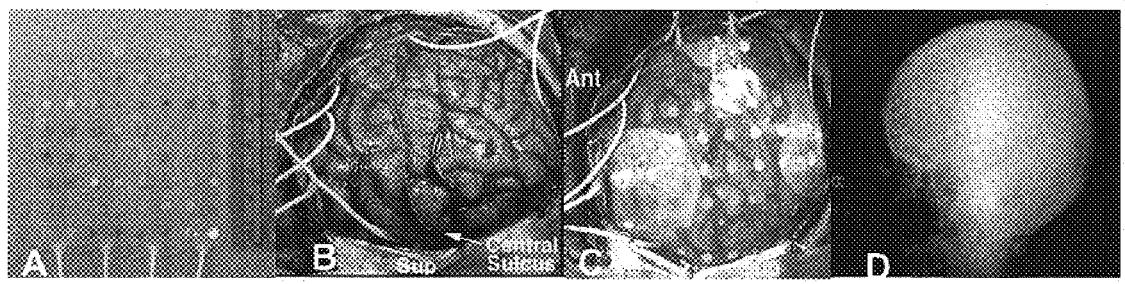
FIG. 4a shows an exemplary subdural electrode grid used in the ECoG-based BCI.
FIG. 4b is shows the exposed cortical surface of a human patient with epilepsy, before placement of the subdural electrode grid.
FIG. 4c shows the placement of the subdural electrode grid over the cortical surface shown in FIG. 4b.
FIG. 4d is an X-ray image of the skull of human patient of FIGS. 4b and 4c, showing the placement of the subdural electrode grid after surgical closure of the scalp.

FIG. 4a is an exemplary subdural electrode grid used in the ECoG-based BCI. Suitable electrode arrays and related hardware are available from, for example, Ad Tech Medical Instrument Corporation (Racine, Wis.), and Radionics (Burlington, Mass.). FIG. 4b shows the exposed cortical surface of a human subject with epilepsy, before placement of the subdural electrode grid shown in FIG. 4a. The arrow indicates the central sulcus in the left hemisphere. FIG. 4c shows the placement of the electrode grid on the exposed cortical surface of the subject. For orientation purposes, the reference "Ant" refers to the anterior of the subject's brain. FIG. 4d is an X-ray image of the subject's skull from one side, showing the electrode grid in place after surgical closure of the subject's scalp.

FIGS. 5a and b demonstrate the analysis of a given subject's single electrode. In FIG. 5a, a spectral analysis is performed to compare an active condition with the inactive or rest condition. In the illustrated case, the active condition is imagining saying the word "move". This example shows a pronounced decrease in power at 20 Hz in the active condition, as compared to the rest condition. The change in power between conditions is then further analyzed using a correlation of determination, or $r^2$, to assess the statistical significance of this change in power. In this example, the $r^2$ is 0.3, indicating that the change in power is highly statistically significant, supporting the inference that whenever this individual imagines saying the word "move", a reliable depression in power exists at 20 Hz.

Figure 5:
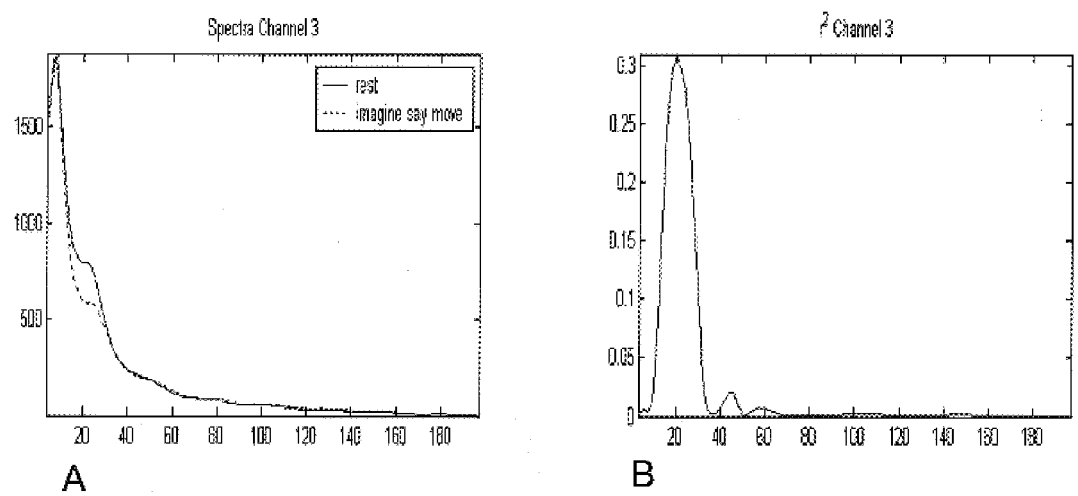
FIG. 5 is a graphical representation of a spectral analysis and analysis of variance of responses from a select electrode location in the electrode array while the human patient is performing a specific task (e.g., imagining saying the word "move" versus rest)
Figure 6:
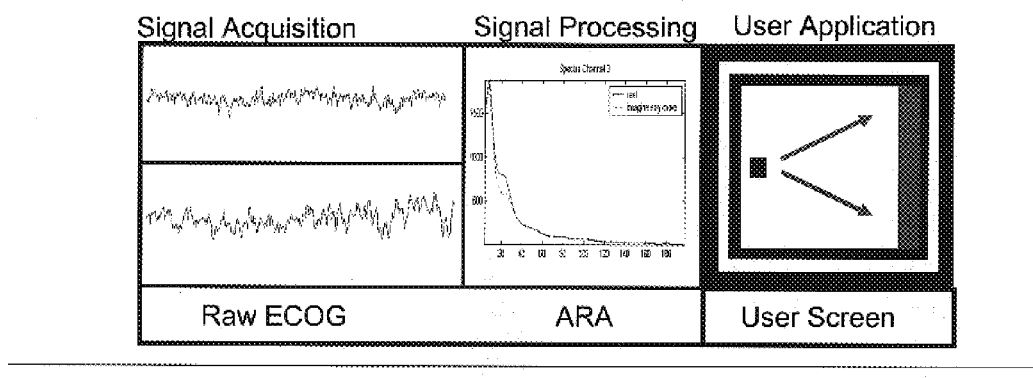
FIG. 6 is a graphical representation of an algorithm used to correlate specific brain signals to specific behavioral conditions of the human patient, using the ECoG-based BCI.

FIG. 6 is a graphical representation of an algorithm used to correlate specific brain signals to specific behavioral conditions of the human patient, using the ECoG-based BCI. As shown supra in FIG. 5, a reliable correlation between a power change at a frequency specific band, once established, is then utilized by the BCI system for device control. In this example, as the BCI system continually acquires raw data from the patient, any point at which the system detects a specific depression in power at 20 Hz (through continued power spectra analysis using a continuous autoregressive analysis, (ARA)) is the basis for generating a signal to direct the cursor upward. In contrast, a baseline level of activity at 20 Hz is the basis for generating a signal for the cursor to be directed downwards.

Figure 7:
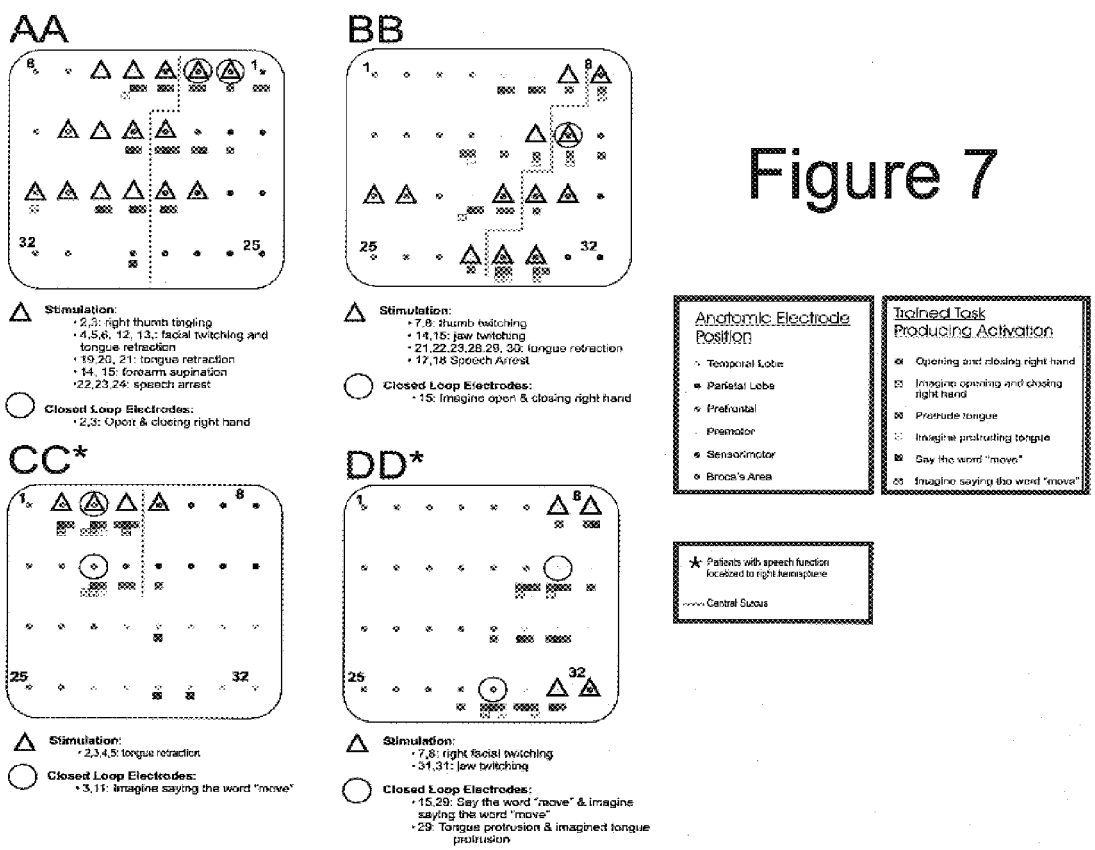
FIG. 7 is a figure correlating cortical anatomy, closed loop electrodes, functional stimulation, and regions of frequency power change induced by various motor, speech, and cognitive activities.

FIG. 7 includes schematic diagrams depicting anatomic location of electrodes, stimulation maps, screening results, and closed loop electrodes for all four subjects (AA, BB, CC, and DD). Lateral skull radiographs were used to determine stereotactic locations of the electrodes. Using a Talairach atlas, the stereotactic locations were mapped to standard Brodmann surface locations. Each electrode is color coded to a standard anatomic surface location as indicated in a first panel at right of FIG. 7. The triangles represent electrodes where overt activity (e.g. motor, sensory, speech) was either induced or suppressed via electrical stimulation. These results are listed below each schematic, respectively. Below each electrode, various tabs indicate whether any statistically significant frequency changes ($r^2 > 0.1$) were induced for a given active condition versus rest, as indicated by the list of active tasks in a second panel at right of FIG. 7. Electrodes used for closed-loop control are circled. The tasks used for closed-loop control are listed below each schematic, respectively.

Protocol for using the ECoG-based BCI involves a screening process, followed by signal feature extraction, and then a process of closing a feedback loop to the user, by which the user adapts control of his conscious instructions to the output of the BCI.

Figure 8:
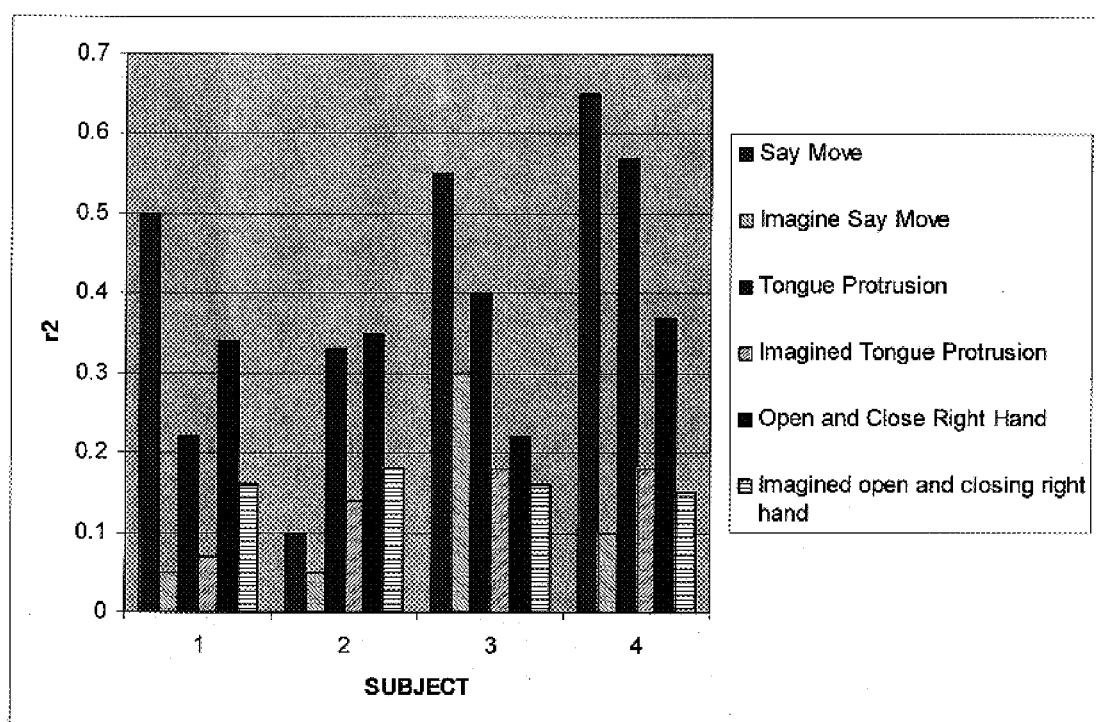
FIG. 8 is a bar graph demonstrating how often a given subject was able to produce statistically significant frequency power changes that could be utilized for online closed loop control.

FIG. 8 is a bar graph demonstrating how often each of the four subjects was able to produce statistically significant frequency power changes that could be utilized for online closed loop control, as indicated by the largest $r^2$ for all frequency bands and locations, for each active task condition. FIG. 8 shows that for the majority of patients and tasks, actual and imagined motor/speech tasks produced task-related spectral changes.

Figure 9:
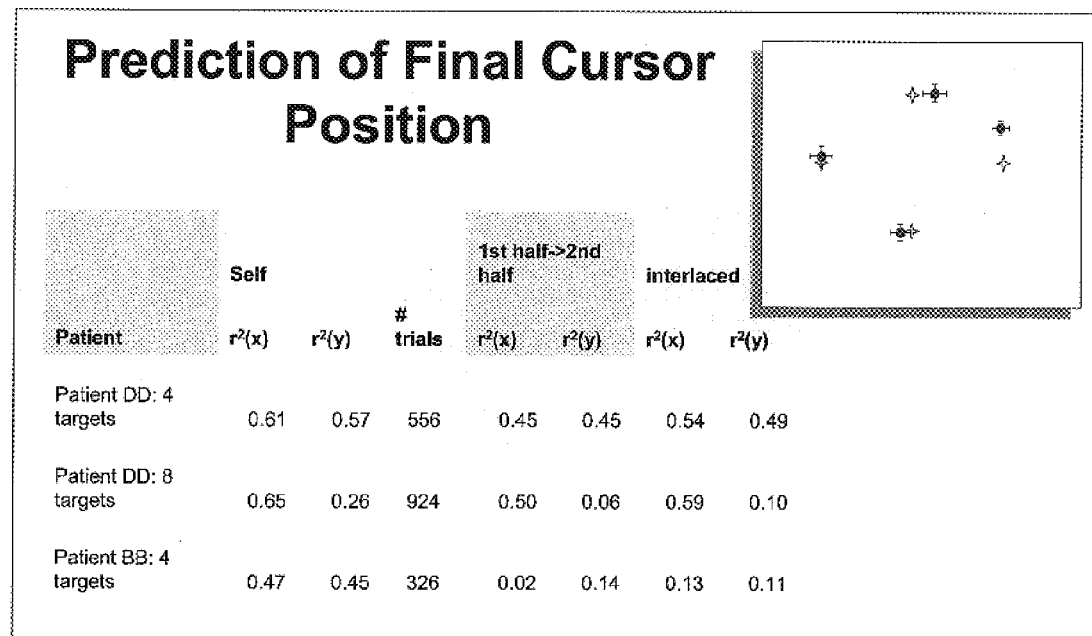
FIG. 9 is a table showing the position of 4 targets predicted from ECoG signal relative to the actual target position using a neural network analysis model.

FIG. 9 shows use of particular features to predict the direction of the actual joystick movement, for subjects BB and DD. The accompanying table delineates the statistical significance of the various modeling methods using both four and eight targets. The predictions were highly correlated with the actual movement directions and generalized to different data sets (see accompanying table). The top right panel of FIG. 9 illustrates the final predicted cursor position (red dots) and the actual target position (yellow stars) for subject DD and four targets.

Figure 10:
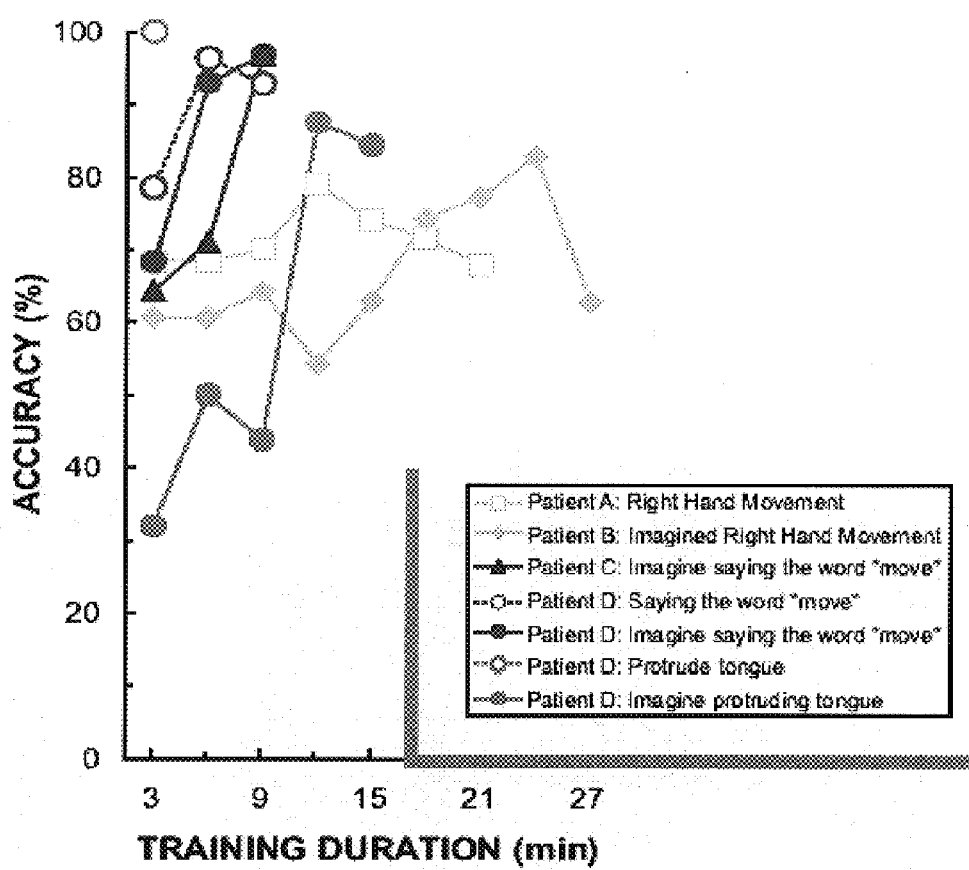
FIG. 10 is a graph showing improvement in human subjects' performance on closed-loop feedback tasks using the ECoG-based BCI.

FIG. 10 shows learning curves for closed-loop experiments. In all subjects, performance improved over a short period (minutes). The solid lines represent imagined tasks while the dashed lines represent actual tasks.

Figure 11:
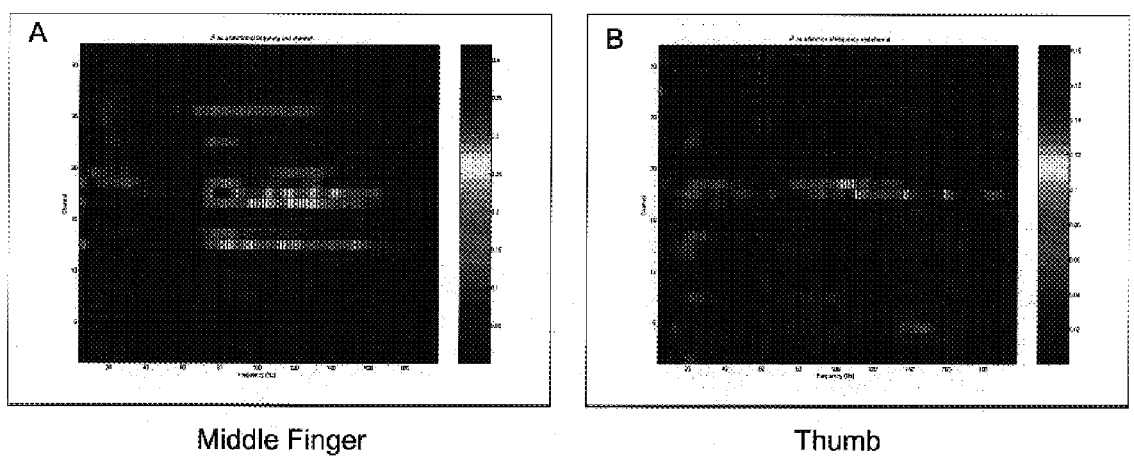
FIG. 11 is a graphical comparison of signal features produced by either (a) middle finger or (b) thumb movement when compared against rest.

FIG. 11 shows results of an analysis of signal variance for the 32 channel arrays. FIG. 11a shows the frequency band changes for active left middle finger movement versus rest (no finger movement). FIG. 11b shows the frequency band changes for active left thumb movement versus rest. Each action of middle finger movement and thumb movement produce different changes with respect to channel and frequency band. This allows for two independent signals to be controlled in parallel to allow for two dimensional control.

In the initial screening process, during training sessions the brain signals of the user are examined and features of the brain signals (i.e., frequencies and locations) that are subject to user control are identified. The training sessions include, for example, multiple simple cognitive tasks that are selected on the basis of their activation of various, specific areas of cortex relative to the location of the electrode grid. Overt tasks are those tasks that require an overt motor output by the user, for example, of a hand, the tongue, or the mouth. Examples of overt tasks are opening and closing of the right hand, tongue protrusion, or saying the word "move". Covert tasks are those that do not involve an overt motor output by the user, but instead require only conscious thought by the user of a specific action. Examples of covert tasks that correlate with the overt tasks previously listed are, respectively, imagining opening and closing the right hand, imagining protruding the tongue, and imagining saying the word "move". Another example of an overt task is manipulation of a joystick to control movement of a screen cursor. Each user is instructed to perform overt and covert tasks.

For each user, the ECoG signals generated during the performance of each task, and during rest, are collected, stored and analyzed. Features of the signals (i.e., signal frequencies and electrode locations) that vary systematically with the user's behavioral state are identified. Software in the BCI system is configured to correlate these features with the user's actions. For example, for each task, the spectral responses for all electrode locations and frequencies (i.e., features) between 0.1 and 220 Hz are compared to the spectral responses under rest conditions. The value of $r^2$, i.e., the proportion of the response variance accounted for by the task, for each of these features is calculated. One or more electrode locations and one or more frequencies that were most closely correlated with a particular task are identified. The analysis of variance is then used to produce a map that identifies the electrode locations and signal frequencies that react to the particular task.

Offline analysis entails, for example, periodically (e.g., 25 times per second) subjecting the ECoG brain signals to autoregressive spectral estimation (McFarland, 1997) that computes the spectral amplitude in a defined frequency range for all locations. A linear classifier then adds the spectral amplitudes for the channels and frequencies that are identified by the previous analyses, after multiplying them by specified weights determined by a user of the system. Subsequently, a linear transformation is performed on each output channel in order to create signals that have zero mean and a specific value range. The output of the normalizer defines the control signal to be used by the output device and represents the output of the signal processing module. An additional statistics component updates in real-time the slope and the intercept of the linear equation that the normalizer applies to each output channel so as to compensate for spontaneous or adaptive changes in the user's brain signals (see Ramoser, 1997; McFarland, 2003).

An exemplary output device is a computer screen. In an exemplary process of adapting to the BCI, the user watches the computer screen. After one second during which the screen is blank, a target appears either on the top or bottom right edge of the computer screen. One second later, a cursor appears on the left edge of the screen, and the cursor travels across the screen at a fixed rate. The cursor's vertical movement is controlled by the control signal calculated by the signal processing component. To the extent that the offline analyses identify a signal that the user can control, the user is then able to control the cursor movement in one dimension.

After the screening protocol and the offline feature extraction and analysis, the BCI computer provides feedback output to the user, and the user is instructed to perform the same task that produced previously identified responses. The user then employs the feedback as a basis for modifying conscious instructions to the output device. In doing so, the user also modifies the device command output, and in an iterative process of calibration ultimately improves the accuracy of the device command and thus the device output, relative to the conscious intent of the user. Finally, a BCI system adapted to a particular user is then employed by the user to more accurately control the output device.

The invention encompasses related methods. An exemplary embodiment is a method for providing control of a device to a user which includes providing an ECoG-based BCI to the user for determining an intent of the user from ECoG signals of the user's brain activity. The BCI determines the intent of the user and then communicates the intent to the device, thereby controlling the device. In one embodiment, a closed-loop feedback arrangement is used to adapt the ECoG-based BCI to the particular user, in which data reflecting the position of the device are provided to the user, and the user periodically compares the target position of the device with the actual position of the device. The user then employs this feedback as a basis for modifying the user's conscious thoughts with respect to control of the device, thereby improving the accuracy of control of the device with the BCI.

EXAMPLES

Without further elaboration, it is believed that one skilled in the art can, using the preceding description, utilize the present invention to its fullest extent. The following specific examples are offered by way of illustration only and not by way of limiting the remaining disclosure.

Example 1

Initial Screening Tasks

An advantage of closed-loop, real-time control is that biofeedback can be used by the brain to adapt the cortical control signal. In order to test ECoG signals in a real-time BCI environment as well as to explore cortical plasticity in a closed-loop ECoG BCI system, subdural electrode grids were utilized in four subjects with intractable epilepsy who underwent temporary array placement to localize seizure foci prior to surgery. The subjects performed a series of motor and cognitive tasks while 32 ECoG channels were digitized and processed with BCI2000 software as described in Schalk et al., *IEEE Trans Biomed Eng.* 10, 1–10 (2003). All subjects were successful at achieving control of the cursor to hit the correct site for a significant percentage of the trials. Likewise, all four subjects showed significant cortical signal adaptation which resulted in an improved cortical control over a period of minutes.

The subjects in this study were patients in the Barnes Jewish Hospital Neurosurgical and Epilepsy program. Subjects were individuals with intractable epilepsy requiring the placement of subdural electrodes for seizure localization. Placement of the electrode arrays was based solely on the clinical judgment of the neurosurgical and epilepsy team;

however, only those candidates who were to have subdural electrodes placed over a portion of sensorimotor cortex were chosen for this study. In all cases involved in this study, a 48 or 64-electrode grid was placed over the left fronto-parietal-temporal region. A standard grid consists of electrodes that are 2 mm in diameter and 10 mm apart. FIG. 4a shows an exemplary electrode grid, and FIGS. 4b, 4c, and 4d show placement of such a grid on the exposed cortical surface of a subject, as described in further detail supra. The four subjects included three males and one female with an average age of 29.8 years ± 6.8 years. See Appendix, Table 1 for additional information. Following initial surgical placement of the subdural electrode all subjects had a post-operative anterior-posterior and lateral radiograph.

Following a standard recovery in the intensive care unit, the subjects were transferred to the epilepsy monitoring unit where the testing for this project occurred. After obtaining written approval from each subject, each performed a series of actual and imagined movement tasks using the BCI 2000 software package. A training session involved 23 runs: seven actual or imagined motor tasks repeated three times each plus two quiescent periods of eyes open and closed. Each run was either 2 or 3 minutes in length separated by a 1 minute break. A run consisted of a set of 30 repeated trials (2–3 seconds in length) of one of the tasks. Subjects were instructed to perform the motor and imagined tasks in response to visual cues (e.g. a red box on a computer screen) presented by a computer running BCI2000. The tasks were performed repetitively during the presence of the visual cue and stopped with its disappearance. During a 65 minute training session, 32 channels of ECoG data were transferred to a microcomputer running BCI 2000 software for signal storage as described in E. E. Sulter, *J. Microcomput. Appl.* 15, 31–45 (1992). Signals were band-pass filtered between 0.1 and 220 Hz and sampled at 500 Hz.

Once the training session was completed, the data was analyzed offline to assess for significant spectral changes for a given task relative to rest (i.e., inter-trial interval). For the joystick task, up versus down, right versus left, and each direction versus rest was also analyzed. The time-series ECoG data was converted into the frequency domain using an autoregressive filter model. The spectra (0–220 Hz) of all the electrodes were initially evaluated. Those electrodes with significant spectral power differences ($r^2 > 0.10$) for each task were identified as potential sources for real-time, closed-loop control of a one-dimensional computer cursor. A decoding algorithm based on a weighted, linear summation of significant spectral frequency bands in various electrodes was generated for testing in the next closed-loop testing session with the subject.

Once significant features of the training session were identified offline, the newly identified decoding algorithm was coded into the BCI2000 system. (Schalk et al., 2003, which is herein incorporated by reference in its entirety). The tasks (e.g. moving hand, protruding tongue, imagined motor task tasks, speech, and imagined speech) were designed such that the resulting processed ECoG signals would direct the cursor upwards as the cursor moved at a fixed speed from the left side to the right side of a computer screen. The rest condition signal was coded such that the cursor would be directed downward as the cursor moved across the screen. For the closed loop session the subject is instructed to use the specific trained movement or imagined task to direct the cursor toward the upper target that appears on the right edge of the screen, and to relax to allow the cursor to go towards the lower target on the right edge of the screen. For a given closed-loop run there were thirty-three trials in which the subject had to direct the cursor towards either the upper or lower target. These were followed by a minute rest period. The number of runs per session was dictated by the subject's willingness to participate. On several subjects, multiple screening and closed-loop sessions were obtained prior to surgical removal of the ECoG grids.

Functional mapping was performed prior to the subject returning to the operating room for removal of the electrode arrays and resection of the epileptogenic foci. The subject underwent stimulation mapping to identify the motor regions and speech cortex. Mapping involved passing 5–10 mA of square wave current through paired electrodes to induce sensory—motor response or speech arrest. Furthermore, the radiographs were used to identify the stereotactic coordinates of each grid electrode and the cortical region defined using Talairach's Co-Planar Stereotaxic Atlas of the Human Brain. The results of the ECoG spectral analysis during the behavioral paradigms, functional electrical stimulus mapping, and stereotactic identification of the electrode locations were collated and analyzed.

During the initial screening task, the subjects performed seven tasks: open and closing their hands, imagining open and closing their hands, tongue protrusion, imagined tongue protrusion, saying the word "move", imagining saying the word "move", and finally a joystick task where the subjects moved a cursor from the center of the computer screen to several (four or eight) radially located targets spaced equally around the initial center position. FIG. 5 shows the results of Subject CC during the imagined "move" task, relative to rest. As seen in panel 2, imagining saying the word "move" produces significantly less power around 20 Hz than rest ($r^2=0.3$, F=36.4, p<0.01). The majority of screening tasks (i.e. open and closing hand, protruding tongue, and saying the word "move") demonstrated statistically significant changes (an $r^2$ of at least 0.1 or greater) when compared to rest in at least one or more electrodes. In addition, the majority of imagined correlates also showed a statistically significant change. (See FIG. 8). The exceptions included the subject who was cognitively impaired due to slow post operative recovery. The optimal of the initial six screening tasks for a given subject was then chosen for subsequent one dimensional, on-line, closed-loop trials.

Beyond the active versus rest comparison in the first six tasks, the final screening task (i.e., joystick task) allowed for spectral comparisons amongst different directions of movement (e.g. up vs down, right vs left). Significant differences in spectral power across directions allowed for off-line prediction of target location in two dimensions. For example, in Subject DD, upward movements demonstrated a statistically significant increase in power in the frequency bands of 51.5–55.5 Hz and 77.5 Hz ($r^2=0.17$ and 0.15 respectively) in electrode 23. With downward movement, on the other hand, electrode 16 demonstrated a statistically significant 51.5–55.5 Hz power increase ($r^2=0.18$). Right and left comparisons also showed statistically significant differences. When compared against leftward movement, directing the cursor rightward demonstrated a significant power elevation in the frequency bands of 63.5–65.5 Hz ($r^2=0.15$) and 85.5–87.5 Hz ($r^2=0.10$) in electrode 16 and a power elevation of 63.5–65.5 Hz ($r^2=0.25$) and 85.5–87.5 Hz ($r^2=0.15$) in electrode 23.

Using a neural network analysis, the power changes of the signals from the electrodes 16 and 23 were then used to assign different weights to various frequency bands from the two channels to predict the position of the cursor relative to the actual cursor position on a Cartesian coordinate system.

FIG. 9 shows the results of a neural network analysis comparing predicted screen cursor position relative to actual cursor position, when four (4) positions were predicted using a weighted ECoG signal. It was found that the four (4) positions, when predicted by the weighted ECoG signal, were distributed in a pattern in which the targets were distinct and in the same relative position to the actual targets. A subsequent additional thirteen (13) runs involving eight (8) targets was then performed and the same weighting system was applied. Again, the individual predicted targets closely approximated the actual final target position.

Example 2

Real Time Closed-Loop Control Using ECoG

All four subjects were able to successfully control the cursor towards a high percentage of the correct target (80–100%) using their ECoG signal in real time and with continuous visual feedback. (Appendix, Table 2). The range of the percentage of optimal correct choices was between 80% and 100% using the various trained tasks. These tasks included motor tasks (i.e. open and closing the right hand, protruding the tongue, and saying the word move) and imagined tasks (i.e. imagining open and closing the hand, imagined tongue protrusion, and imagining saying the word "move"). All subjects were able to achieve control within minutes following their initial sixty-five (65) minute training session.

The ECoG frequency bands utilized to achieve control were different for different subjects. They encompassed a broad range of alpha, beta, and high and low gamma frequencies. In general, the controlling frequencies showed power suppression in the alpha and beta frequency ranges and power increases in the higher gamma ranges.

FIG. 10 shows improvement in human subjects' performance on a closed-loop feedback task using the ECoG-based BCI. Each subject's performance improved during the course of their closed loop session. As the session progressed, there was a trend for increasing percentage of correct targets. When an analysis of variance was performed following the session, there was a trend in all subjects to show a steady increase in $r^2$ between the two conditions of the cursor moving up and down. The optimal $r^2$ achieved for the various closed loop trial between subjects was between 0.22 and 0.90. The computer was made to adapt only with respect to dynamic range and gain of the signal. Therefore, a certain portion of the improvement is attributable to changes in cortical activity, as described in more detail in Ramoser et al., 1997.

A novel BCI and related methods are based on the surprising results set forth in the Examples which demonstrate real time, on-line control of a cursor in one dimension using electrocorticographic signal. Closed loop trials were accomplished with minimal training, achieved control within minutes, and utilized novel tasks and novel frequency bands to achieve control. A high level of control (80–100%) was performed irrespective of the subject's functional status and enabled use of a broad range of frequencies ranging from as low as 11.5 Hz to as high as 53.5 Hz. Additionally, each subject, during his or her closed loop session, demonstrated trends towards improved correct target choice with repetition of runs. Further analysis of this increase in performance confirmed that this was a reflection of cortical adaptation to adjust the ECoG signal between the two conditions of up and down. Moreover, this adaptation occurred very rapidly on the order of minutes, which places ECoG signal tuning time in the same range as that of single unit systems rather than the weeks to months required for EEG based systems.

The overt control achieved by the various subjects is notable in that both standard tasks (actual and imagined motor activity) and novel tasks (actual and imagined speech) were used. Concomitantly, the cortex activated in these closed loop sessions involved regions of sensorimotor cortex as expected, but also involved areas such as the premotor cortex and Broca's area. Subjects AA and BB had a fair degree of concordance in their hand related tasks. While AA performed the actual motor task of hand opening and closing, BB performed the imagined version. The electrodes of both AA and BB's were positioned in Brodman's areas 2 and 3. Subjects CC and DD both used speech to control the cursor position (subject DD utilized both actual and imagined speech, and subject CC used imagined speech only). Both subjects CC and DD required the use of two electrodes for closed loop control. Each subject CC and DD had an electrode that was found to be in Brodman's areas 44/45, or Broca's area. While performing tongue protrusion alone, Subject DD involved a single electrode in area 44, but not in 6 as found with the speech paradigm. That the brain signals underlying these novel tasks were distributed over a limited region of cortical space, involving various areas of functional cortex, shows both the improved spatial and signal resolution of ECoG signal and supports multiple degrees of freedom of control within a limited cortical region.

Multiple degrees of freedom of user control is a goal of any BCI. Discussions of degrees of freedom of user control with respect to user brain signals other than ECoG are provided in, for example, Fetz and Finocchio (1971) (first demonstrated one degree of control obtained from operant training of a monkey to alter the firing rate of a single neuron); Wolpaw et al., (1991)(using EEG signal from scalp electrodes in humans); Kennedy and Bakay, (1998) (utilizing glass cone electrodes in a human ALS patient); Wessberg et al. (2000)(using multiple microelectrode arrays in monkeys); Serruya et al. (2002) (achieving two degrees of freedom of control in monkeys using microelectrode arrays); Taylor et al., (2002) (achieving three dimensional, currently the highest level of control, using microelectrode arrays in primates).

To assess the degree of information that may lie nascent in the ECoG signal for describing position in space, an analysis was performed offline with the data acquired from the four and eight target joystick tasks of subject ES. Using the ECoG data acquired from two electrodes that showed significant changes during joystick manipulation, the power changes were analyzed using a neural network analysis. The frequency bands were within the high gamma range and changes associated with movement were associated with power increases. For both four and eight target trials the analysis showed significant correlation to the actual final target positions. The relationship between predicted and actual targets is shown in FIG. 9. Though performed offline, this analysis supports the idea that directional ECoG signal supplies the information necessary for two dimensional control.

Example 3

Achieving Two-Dimensional Online control

In addition to mapping out two dimensional information as a method for achieving two-dimensional (2D) control, another method involves the use of two independently controlled signals in parallel. This was achieved in one subject in which analysis demonstrated the ability to separate out the signal information for individual finger movements. In this particular example, signal differences were observed between the middle finger and the thumb. Specifically, the middle finger produced frequency power changes in channels 12, 16, 17 and 25. These frequencies were predominantly between 70 and 160 HZ. In contrast, the thumb produced significant frequency changes predominantly in channels 17 and 18, with frequency band changes in the 60–170 Hz and 100–110 Hz ranges respectively. (FIG. 11). By taking the channels and frequency bands that were distinct to each finger, namely channel 12 at 80–160 Hz for the middle finger, and channel 18 at 100–110 Hz for the thumb respectively, the subject could then differentially control movement in different directions by moving either the middle finger or the thumb. Thus, each finger was able to control a given direction. When held immobile and pointing to the left (inactive condition), the left thumb directed the cursor to the left. When actively pointed to the right (active condition), the left thumb directed the cursor to go left. The left middle finger held immobile and pointing up (inactive condition) directed the cursor upwards, and the left middle finger actively pointing downwards (active condition) directed the cursor to go downwards.

After a brief training session the subject was able to achieve a high level of two-dimensional control with an optimal target accuracy of 88% and 94% for two separate sessions. Additionally, two-dimensional control was achieved using motor imagery alone. The subject was asked to imagining various parts of his left arm. These included the fingers, the hand, and the arm at the shoulder. Analysis was once again performed in which the active imagined conditions were compared against rest. The most notable active conditions, and also the most independent, were the imagined shoulder movement and imagined middle finger movement. For the imagined shoulder task significant increases in power were noted between 80 and 110 Hz in channel 28, while the imagined finger task produced significant power decreases in the 20–30 Hz range in channel 18. These tasks were then coded into the BCI computer such that the active imagined condition of imagining shoulder movement moved the cursor to the right (with an increase in power in channel 28 at 80–110 Hz). Imagining the shoulder held still moved the cursor left (decrease in power in channel 28 at 80–110 Hz). To move the cursor down, the patient imagined moving the finger (decrease in power in channel 18 at 30 Hz), and to move the cursor up the patient imagined the finger being held erect (increase in power in channel 18 at 30 Hz). The patient performed two sessions using these imagined task and was able to achieve control with optimal target accuracy of 70% and 82%.

The ability to separate individual finger movements and limb movements has not previously been achieved utilizing EEG or other BCI technology In addition, the use of individual finger movement and limb movement to achieve two dimensional control has not previously been shown. In particular, the signal frequencies involved in the present invention are well outside the technical limitations of EEG-based techniques. Thus, the inventors have successfully demonstrated the novel use of ECoG in a BCI system to discriminate various individual finger movements and limb movements, which is especially useful as a basis for providing multiple dimensions of external device control.

Further, the regional discrimination by ECoG acquisition is finer than what is achievable using EEG (millimeters for ECoG versus centimeters for EEG). With the combination of higher spatial resolution, better signal to noise ratios, broader frequency range sensitivity, and lower clinical risk (relative to single unit systems), ECoG signal is especially well-suited to BCI applications. The results set forth in the Examples are the first demonstration of use of this signal for closed-loop control. That the demonstrated results were achieved within minutes of initiation of online trials following minimal training, combined with evidence that the signal provides information on two dimensional space, and that two dimensional online control was achieved utilizing previously undiscovered differences in ECoG signal between individual fingers, advances ECoG as a novel BCI platform for human applications.

OTHER EMBODIMENTS

The cognitive basis of human speech and language is an important and continuing area of neuroscience research. The known radiographic and electrophysiologic techniques described supra have been applied to the studying the neural bases of human language, and the results have subsequently challenged some of the classical interpretation of the Wernicke-Lichtheim model of speech in which there is a center for language production (Broca's area) and center for conceptual understanding (Wernicke's area). Petersen et al. (1988), first utilized PET to assess various elements of language processing at the single word level from passive word viewing, to noun reading/repetition, to verb generation tasks. The results were somewhat surprising in that noun reading/repetition did not activate Wernicke's or Broca's area to any extent, and the tasks involved with more complex language processing (verb generation) were most associated with activation in the left inferior frontal cortex or Broca's area. Previously this region had conventionally been associated with the motor programming of speech but not with higher semantic processing. Conflicting with this view, Wise et al. (1991) found semantic processing in both Broca's and Wernicke's locations. Further, other groups using PET and fMRI later reported findings similar to those previously reported by Petersen et al. (1988), showing activation of Broca's region by various overt and covert speech tasks.

Various electrophysiological paradigms have also been used to investigate the role of inferior frontal lobe and rolandic cortex with semantic processing. Crone et al. (1994) found 8–13 Hz suppressions associated with picture-naming in the posterior frontal lobe. Additionally, Crone et al., (2001), found increased gamma band activity for three different spoken and hand signed language tasks in the same region over the left inferior frontal gyrus. Ihara et al., (2003), utilized MEG ERPs and found that syntactic word processing of words was centered in the inferior frontal sulcus and the precentral sulcus. Collectively the results of these studies suggest that the classically understood Broca's region may perform cognitive functions beyond simple motor programming of speech.

To demonstrate aspects of the BCI of the present invention, the examples described herein were directed toward characterizing differences in the electrophysiology between linguistic and non-linguistic articulation in Broca's area. Electrocorticographic signal was acquired from three subjects with intractable epilepsy who required the placement of subdural electrode arrays over the fronto-temporal-parietal region. To examine both the motor and semantic properties of language in Broca's region, the paradigm that was employed involved comparing ECoG signals generated during oral motor tasks, repetitive speech tasks, and verb generation tasks.

Acquisition of ECoG signals in a real-time, time locked fashion using the BCI device allows one to investigate human and non-human cortical activity, but is especially useful for human applications. Previously, examining ECoG signals in humans was an extremely difficult process because, while data could be acquired from data storage, it was impossible to synchronize or "tag" the recorded data in time with a given behavioral/motor/cognitive paradigm. In other words, it was very difficult to know exactly when the individual may have been gotten a cue to do something, such as saying a word, moving their hand, or doing some other task. Also it was difficult to know, not only when they got the cue, but when they actually responded to a given cue. Since ECoG changes occur on the order of milliseconds, the lack of precise time synchronization between cues, responses, and ECoG recording previously made it very difficult to extract information about how changes in ECoG activity correlate with behavior, motor activity, cognition, etc.

In contrast, the BCI system of the present invention provides a relatively easy means for extracting information from ECoG activity that correlates with behavior, motor activity, and cognition. The recording of ECoG is done in real time, and the cues for various tasks and behavioral responses are all coordinated within a single system that is running BCI software (BCI2000) that is customized to tag all the data relating to cues and other aspects of the behavioral state. Accordingly, all the data can be parsed for future analysis, which allows for very detailed investigation that was previously very difficult. The system and methods permit one to know exactly what changes in the ECoG signal occurred before, during, and after a given event, regardless of whether that event is a cue to act, an image presented for cognitive response, or an overt or covert behavioral response of some sort (verbal, motor, cognitive, emotional).

In applying this to the experimental paradigm used to demonstrate the BCI of the present invention, in which various types of speech tasks ranging from simple motor, to repetitive, to more complex, were performed, various cognitive functions were differentiated both in terms of anatomic location, but also in regard to frequency band.

FIG. 12 provides an example of one of three subjects' topograms of regional frequency changes at 18 Hz (left column) and 40 Hz (right column) with a given task such as tongue protrusion (top row), repetitive speech (middle row), and verb generation (bottom row). The white line represents the central sulcus and the gray line outlines Broca's area. The first two rows show regions of frequency change around the central sulcus, namely sensorimotor cortex. The higher linguistic function, or verb generation, however, demonstrates distinctly different regions of frequency power change located in the inferior frontal region. Moreover, this change in regional frequency power change occurs primarily at 18 Hz and not in other frequencies (such as 40 Hz—the right column). These findings suggest that inferior frontal cortex are involved with higher cognitive function and that this information may somehow be conveyed at frequency power changes at around 18 Hz.

These results show that the BCI of the present invention not only deciphers intent for generating an overt device command, but also deciphers the meaning of ECoG signal as it relates to various brain activities.

Furthermore, the real time capacity of the BCI system allows for a truly novel method of assessing cortical function from a fundamentally causal perspective. All previously available methods (fMRI, PET, EEG) look at phenomena such as blood flow changes and frequency power changes in association with a given cognitive activity. Associations between a given cognitive activity and some type of statistically significant change in signal provide the bases for conclusions that the change in signal indicates involvement in the given cognitive activity. In contrast, in a system in which a real time brain signal (i.e. ECoG) is utilized for overt control of a device, the signal is definitively involved with a given cognitive process in order to achieve device control. In other words, once real time control is achieved using a defined signal with a defined cognitive process, the signal is demonstrably causal to control of the device and therefore is definitively involved with the given cognitive activity utilized for device control. Thus, in contrast to previously known techniques and approaches, the BCI and related methods of the present invention provide new tools for delineating brain function.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

REFERENCES

Wolpaw, J. R., Birbaumer, N., McFarland, D. J., Pfurtscheller, G., Vaughan, T. M. Brain-computer interfaces for communication and control. *Clin Neurophysiol.* 113, 767–791 (2002)

Vidal, J. J. Real time detection of brain events in EEG. *IEEE Proc.* 65, 663–664 (1977).

Sutter E. E. The brain response interface: communication through visually induced electrical brain responses. *J Microcomput Appl.* 15, 31–45 (1992).

Elbert T., Rockstroh B., Lutzenberger W., Birbaumer N. Biofeedback of slow cortical potentials. I. *Electroencephalogr Clin Neurophysiol.* 48, 293–301 (1980)

Farwell L. A., Donchin E. Talking off the top of your head: toward a mental prosthesis utilizing event-related brain potentials. *Electroencephalogr Clin Neurophysiol.* 70, 510–23 (1988).

Wolpaw J. R., McFarland D. J., Neat G. W., Forneris C. A. An EEG-based brain-computer interface for cursor control. *Electroencephalogr Clin Neurophysiol.* 78, 252–9 (1991).

Pfurtscheller G., Flotzinger D., Kalcher J. Brain Computer Interface—a new communication device for handicapped persons. *J Microcomput Appl.* 16, 293–299 (1993).

Georgopoulos A. P., Schwartz A. B., Kettner R. E. Neuronal population coding of movement direction. *Science.* 233, 1416–9 (1986).

Laubach M., Wessberg J., Nicolelis M. A. Cortical ensemble activity increasingly predicts behaviour outcomes during learning of a motor task. *Nature.* 405, 567–71 (2000).

Taylor D. M., Tillery S. I., Schwartz A. B. Direct cortical control of 3D neuroprosthetic devices. *Science.* 296, 1829–32 (2002)

Kennedy P. R., Bakay R. A. Restoration of neural output from a paralyzed patient by a direct brain connection. *Neuroreport.* 9, 707–11 (1998).

Boulton A. A., Baker G. B., Vanderwolf C. H., eds. *Neurophysiological Techniques: Applications to Neural Systems.* Humana Press, Totowa, 1–58 (1990).

Freeman W. J., Holmes M. D., Burke B. C., Vanhatalo S., Spatial spectra of scalp EEG and EMG from awake humans. *Clin Neurophysiol* 114, 1053–1068 (2003).

Srinivasan R, Nunez P L, Silberstein R B. Spatial filtering and neocortical dynamics: estimates of EEG coherence. *IEEE Trans Biomed Eng.* 45, 814–26 (1998).

Wolpaw J. R., McFarland D. J., Vaughan T. M. Brain-computer interface research at the Wadsworth Center. *IEEE Trans Rehabil Eng.* 8, 222–6 (2000).

Pfurtscheller G., Neuper C., Guger C., Harkam W., Ramoser H., Schlogl A., Obermaier B., Pregenzer M., Current trends in Graz Brain-Computer Interface (BCI) research. *IEEE Trans Rehabil Eng.* 8, 216–9 (2000).

Kostov A., Polak M. Parallel man-machine training in development of EEG-based cursor control. *IEEE Trans Rehabil Eng.* 8, 203–5 (2000).

Lopes da Silva F. Neural mechanisms underlying brain waves: from neural membranes to networks. *Electroencephalogr Clin Neurophysiol.* 79, 81–93 (1991).

Pfurtscheller G., Lopes da Silva F. H. Event-related EEG/MEG synchronization and desynchronization: basic principles. *Clin Neurophysiol.* 110, 1842–57 (1999).

McFarland D. J., Miner L. A., Vaughan T. M., Wolpaw J. R. Mu and beta rhythm topographies during motor imagery and actual movements. *Brain Topogr.* 12, 177–86 (2000).

Crone N. E., Miglioretti D. L., Gordon B., Sieracki J. M., Wilson M. T., Uematsu S., Lesser R. P. Functional mapping of human sensorimotor cortex with electrocorticographic spectral analysis. I. Alpha and beta event-related desynchronization. *Brain.* 121, 2271–99 (1998).

Pfurtscheller G., Graimann B., Huggins J. E., Levine S. P., Schuh L. A. Spatiotemporal patterns of beta desynchronization and gamma synchronization in corticographic data during self-paced movement. *Clin Neurophysiol.* 114, 226–36 (2003).

Crone N. E., Miglioretti D. L., Gordon B., Lesser R. P. Functional mapping of human sensorimotor cortex with electrocorticographic spectral analysis. II. Event-related synchronization in the gamma band. *Brain.* 121, 2301–15 (1998).

Aoki F., Fetz E. E., Shupe L., Leftich E., Ojemann G. A. Increased gamma-range activity in human sensorimotor cortex during performance of visuomotor tasks. *Clin Neurophysiol.* 110, 524–37 (1999).

Levine S P, Huggins J E, BeMent S L, Kushwaha R K, Schuh L A, Passaro E A, Rohde M M, Ross D A. Identification of electrocorticogram patterns as the basis for a direct brain interface. *J Clin Neurophysiol.* 6, 439–47 (1999).

Huggins J E, et. al. Detection of event-related potentials for development of a direct brain interface. *J Clin Neurophysiol.* 16, 448–55 (1999).

Levine S. P., et al. A direct brain interface based on event-related potentials. *IEEE Trans Rehabil Eng.* 8, 180–5 (2000).

Rohde M. M., et al. Quality estimation of subdurally recorded, event-related potentials based on signal-to-noise ratio. *IEEE Trans Biomed Eng.* 49, 31–40 (2002).

Schalk G., McFarland D. J., Hinterberger T., Birbaumer, N., Wolpaw J. R. BCI2000: A general purpose brain computer interface (BCI) system for research and development. *IEEE Trans Biomed Eng* 10, 1–10 (2003)

Schalk G., McFarland D. J., Hinterberger T., Birbaumer, N., Wolpaw J. R. BCI2000: A general purpose brain computer interface (BCI) system for research and development. *IEEE Trans Biomed Eng* 10, 1–10 (2003)

Schalk G., McFarland D. J., Hinterberger T., Birbaumer, N., Wolpaw J. R. BCI2000: A general purpose brain computer interface (BCI) system for research and development. *IEEE Trans Biomed Eng* 10, 1–10 (2003)

Fox P. T., Perlmutter J. S., Raichle M. E., A stereotactic method of anatomical localization for positron emission tomography. *J Comput Assist Tomogr.* 9, 141–53 (1985).

Ramoser H., Wolpaw J. R., Pfurtscheller G. EEG-based communication: evaluation of alternative signal prediction methods, *Biomedizinische Technik.* 42, 226–33 (1997).

Wolpaw J. R., McFarland D. J., Neat G. W., Forneris C. A. An EEG-based brain-computer interface for cursor control. *Electroencephalogr Clin Neurophysiol.* 78, 252–9 (1991).

Wolpaw J. R., Mcfarland D. J., Vaughan T. M., Brain-computer interface research at the Wadsworth Center. *IEEE Trans Rehabil Eng.* 8, 222–225 (2000)

Fetz E. E., Finocchio D. V., Operant conditioning of specific patterns of neural and muscular activity. *Science.* 174, 431–5 (1971).

Neuper C., Muller G. R., Kubler A., Birbaumer N., Pfurtscheller G., Clinical application of an EEG-based brain-computer interface: a case study in a patient with severe motor impairment. *Clin Neurophysiol.* 114, 399–409 (2003).

Wolpaw J. R., Flotzinger D., Pfurtscheller G., McFarland D. J., Timing of EEG-based cursor control. *J Clin Neurophysiol.* 14, 529–38 (1997).

Penny W. D., Roberts S. J., Curran E. A., Stokes M. J., EEG-based communication: pattern recognition approach. *IEEE Trans Rehabil Eng.* 8, 214–5 (2000).

Kubler A., Kotchoubey B., Hinterberger T., Ghanayim N., Perelmouter J., Schauer M., Fritsch C., Taub E., Birbaumer N., The thought translation device: a neurophysiological approach to communicationin total motor paralysis. *Exp Brain Res.* 124, 223–32 (1999).

Neuper C., Schlogl A., Pfurtscheller G., Enhancement of left-right sensorimotor EEG differences during feedback-regulated motor imagery. *J Clin Neurophysiol.* 16, 373–82 (1999).

Wessberg J., Stambaugh C. R., Kralik J. D., Beck P. D., Laubach M., Chapin J. K., Kim J., Biggs S. J., Srinivasan M. A., Nicolelis M. A., Real-time prediction of hand trajectory by ensembles of cortical neurons in primates. *Nature.* 408, 361–5 (2000).

Wolpaw J. R., McFarland D. J., Multichannel EEG-based brain-computer communication. *Electroencephalogr Clin Neurophysiol.* 90, 444–9 (1994).

Serruya M. D., Hatsopoulos N. G., Paninski L., Fellows M. R., Donoghue J. P., Instant neural control of a movement signal. *Nature*. 416, 141–2 (2002).

Taylor D. M., Tillery S. I., Schwartz A. B., Direct cortical control of 3D neuroprosthetic devices. *Science*. 296, 1829–32 (2002).

Grabowski, T. J., Damasio, A. R. (2000). Investigating Language with Functional Neuorimaging. In Brain Mapping The Systems, A. W. Toga and J. C. Mazziotta, eds. (San Diego Calif.: Academic Press), pp. 425–458.

Villringer, A., and Dirnagl, U. (1995). Coupling of brain activity and cerebral blood flow: basis of functional neuroimaging. Cerebrovasc Brain Metab Rev 7, 240–76.

Jueptner, M., Weiller, C. (1995) Review: does measurement of regional cerebral blood flow reflect synaptic activity? Implications for PET and fMRI. Neuroimage 2, 148–56.

Turner, R., Howseman, A., Rees, G. E., Josephs, O., Friston, K. (1998) Functional magnetic resonance imaging of the human brain: data acquisition and analysis. Exp Brain Res 123, 5–12.

Di Salle, F., Formisano, E., Linden, D. E., Goebel, R., Bonavita, S., Pepino, A., Smaltino, F., Tedeschi, G. (1999) Exploring brain function with magnetic resonance imaging. Eur J Radiol 30, 84–94.

Mathiesen, C., Caesar, K., Akgoren, N., Lauritzen, M. (1998) Modification of activity-dependent increases of cerebral blood flow by excitatory synaptic activity and spikes in rat cerebellar cortex. J Physiol 15, 555–66.

Peyron, R., Le Bars, D., Cinotti, L., Garcia-Larrea, L., Galy, G., Landais, P., Millet, P., Lavenne, F., Froment, J. C., Krogsgaard-Larsen, P., et al. (1994) Effects of GABA-A receptors activation on brain glucose metabolism in normal subjects and temporal lobe epilepsy (TLE) patients. A positron emission tomography (PET) study. Part I: Brain glucose metabolism is increased after GABA-A receptors activation. Epilepsy Res 19, 45–54.

Peyron, R., Cinotti, L., Le Bars, D., Garcia-Larrea, L., Galy, G., Landais, P., Millet, P., Lavenne, F., Froment, J. C., Krogsgaard-Larsen, P., et al. (1994) Effects of GABA-A receptors activation on brain glucose metabolism in normal subjects and temporal lobe epilepsy (TLE) patients. A positron emission tomography (PET) study. Part II: The focal hypometabolism is reactive to GABAA agonist administration in TLE. Epilepsy Res 19, 55–62.

Roland, P. E., Friberg, L. (1988) The effect of the GABA-A agonist THIP on regional cortical blood flow in humans. A new test of hemispheric dominance. J Cereb Blood Flow Metab 8, 314–23.

Tagamets, M. A., Horwitz, B., (2001) Interpreting PET and fMRI measures of functional neural activity: the effects of synaptic inhibition on cortical activation in human imaging studies. Brain Res Bull 54, 267–73.

Petersen, S. E., Fox, P. T., Posner, M. I., Mintun, M., Raichle, M. E. (1988) Positron emission tomographic studies of the cortical anatomy of single-word processing. Nature 331, 585–9.

Raichle, M. E. (1996) What words are telling us about the brain. Cold Spring Harb Symp Quant Biol 61, 9–14.

Pfurtscheller, G. (1977) Graphical display and statistical evaluation of event-related desynchronization (ERD). Electroencephalogr Clin Neurophysiol 43, 757–60.

Pfurtscheller, G., Berghold, A. (1989) Patterns of cortical activation during planning of voluntary movement. Electroencephalogr Clin Neurophysiol 72, 250–8.

Pfurtscheller G., Graimann B., Huggins J. E., Levine S. P., Schuh L. A. Spatiotemporal patterns of beta desynchronization and gamma synchronization in corticographic data during self-paced movement. *Clin Neurophysiol.* 114, 226–36 (2003).

Pfurtscheller, G. (1992) Event-related synchronization (ERS): an electrophysiological correlate of cortical areas at rest. Electroencephalogr Clin Neurophysiol 83, 62–9.

Singer, W. (1993) Synchronization of cortical activity and its putative role in information processing and learning. Annu Rev Physiol 55, 349–74.

Crone, N. E., Boatman, D., Gordon, B., Hao, L. (2001) Induced electrocorticographic gamma activity during auditory perception. Brazier Award-winning article, 2001. Clin Neurophysiol 112, 565–82.

Pfurtscheller G, Cooper R. (1975) Frequency dependence of the transmission of the EEG from cortex to scalp. Electroencephalogr Clin Neurophysiol 38, 93–6.

Roberts, T. P., Poeppel, D., Rowley, H. A. (1998) Magnetoencephalography and magnetic source imaging. Neuropsychiatry Neuropsychol Behav Neurol 11, 49–64.

Freeman W. J., Holmes M. D., Burke B. C., Vanhatalo S., Spatial spectra of scalp EEG and EMG from awake humans. *Clin Neurophysiol* 114, 1053–1068 (2003).

Bookheimer, S. Y., Zeffiro, T. A., Blaxton, T. A., Gaillard, P. W., Theodore, W. H., (2000) Activation of language cortex with automatic speech tasks. Neurology 55, 1151–7.

Friedman, L., Kenny, J. T., Wise, A. L., Wu, D., Stuve, T. A., Miller, D. A., Jesberger, J. A., Lewin, J. S. (1998) Brain activation during silent word generation evaluated with functional MRI. Brain Lang, 64, 231–56.

Palmer, E. D., Rosen, H. J., Ojemann, J. G., Buckner, R. L., Kelley, W. M., Petersen, S. E. (2001) An event-related fMRI study of overt and covert word stem completion. Neuroimage 14, 182–93.

Yetkin, F. Z., Hammeke, T. A., Swanson, S. J., Morris, G. L., Mueller, W. M., McAuliffe, T. L., Haughton, V. M. (1995) A comparison of functional MR activation patterns during silent and audible language tasks. AJNR Am J Neuroradiol 16, 1087–92.

Binder J R. (1997) Neuroanatomy of language processing studied with functional MRI. Clin Neurosci, 4, 87–94.

Crone N. E., Hart. J., Boatman D., Lesser, R. P., Gordon, B. (1994) Regional cortical activation during language and related tasks identified by direct cortical electrical recording. Brain Lang 47, 466–468.

Crone, N. E., Hao, L., Hart, J., Boatman, D., Lesser, R. P., Irizarry, R., Gordon, B. (2001) Electrocorticographic gamma activity during word production in spoken and sign language. Neurology 57, 2045–53.

Ihara, A., Hirata, M., Sakihara, K., Izumi, H., Takahashi, Y., Kono, K., Imaoka, H., Osaki, Y., Kato, A., Yoshimine, T., Yorifuji, S. (2003) Gamma-band desynchronization in language areas reflects syntactic process of words. Neurosci Lett 339, 135–8.

TABLE 1

Table 1. Patient Profiles

| Subject | Age | Sex | Seizure etiology & type | Grid Placement | Electrode # | Seizure Focus |
|---------|-----|-----|-------------------------|----------------|-------------|---------------|
| AA | 28 | M | Idiopathic GTC | Left FTP | 64 | Left posterior temporal lobe |
| BB | 23 | M | Idiopathic CP | Left FTP | 64 | Left middle temporal lobe |
| CC | 35 | F | Idiopathic CP | Left FTP | 38 | Left inferior and mesial temporal lobe |
| DD | 33 | M | Idiopathic CP>C | Left Inferior FP and temporal | 64 | Left middle and posterior temporal lobe |

Abbreviations: M, male; F, female; GTC, general tonic clonic; CP, complex partial; FTP, frontal-temporal-parietal; FP, frontal-parietal.

TABLE 2

Table 3. Signal features of closed loop sessions

| Subject | Cognitive Capacity | Action | Electrodes involved | Frequency Bands | Frequency Change | Brodman's Areas** | Optimal Performance*** |
|---------|--------------------|--------|---------------------|-----------------|------------------|-------------------|------------------------|
| AA | Severely impaired | Open and closing right hand | 2, 3 | (2) 11.5–17.5 Hz 49.5–53.5 Hz (3) 31.5–33.5 Hz 49.5–51.5 Hz | Decrease Increase Increase Increase | 2, 3 | 80% |
| BB | High Functioning | Imagine open and closing right hand | 15 | 31.5 Hz | Decrease | 3 | 83% |
| CC | High Functioning | Imagine saying move | 3, 11 | 21.5 Hz | Decrease | 9, 44 | 97% |
| DD | Mildly impaired | Say Move & imagine saying move | 15, 29 | 13.5 Hz 27.5 HZ 35.5 Hz | Decrease Decrease Decrease | 6, 45 | 96% & 97% |
| | | Tongue Protrusion & Imagined Tongue protrusion | 29 | 13.5 Hz | Decrease | 45 | 100% & 88% |

**Calculated using skull radiographs and a Talairach atlas◊
***Maximal percentage of correct of two targets chosen
◊Talairach, J., Tournoux P., Co-Planar Stereotaxic Atlas of the Human Brain. Thieme Medical Publischers, Inc., New York (1998).

What is claimed is:

1. A brain computer interface (BCI) comprising:
   an electrocorticography (ECoG) electrode array adapted to be implanted beneath the scalp of a user and configured for acquiring electrocorticography (ECoG) signals of the subject;
   an acquisition computer coupled to the electrode array for collecting and storing the ECoG signals; and,
   coupled to the acquisition computer, a BCI computer having software configured to analyze the ECoG signals to determine an intent of the user.

2. A BCI according to claim 1 further comprising an output device communicatively coupled to the BCI computer, the BCI computer further configured to generate a device command from the intent of the user.

3. A BCI according to claim 1 wherein said electrode array provides signals of mu, beta and gamma rhythms of the user.

4. A BCI according to claim 1 wherein said electrode array provides signals having a significant frequency content (power) of greater than about 40 Hz.

5. A brain computer interface BCI comprising acquisition hardware for acquiring an ECoG signal communicatively coupled to a BCI computer configured to analyze the ECoG signal to determine an intent of a user.

6. A BCI according to claim 5 further comprising an output device communicatively coupled to the BCI computer, the BCI computer further configured to generate a device command from the intent of the user, to control the output device.

7. A method for providing control of an output device by a user comprising:
   collecting ECoG signals of the user's brain activity using an electrocorticography (ECoG) based brain computer interface (BCI); and
   computer processing the ECoG signals to determine an intent of the user with respect to the output device.

8. A method according to claim 7 comprising:
   generating from the intent of the user a device command to the output device;
   communicating the device command to the output device.

9. A method according to claim 8 further comprising:
   monitoring a position of the output device; and
   providing feedback to the user on the position of the output device with respect to a target position.

10. A method according to claim 8 wherein monitoring the brain activity of the user comprises monitoring mu, beta and gamma rhythms of the user.

11. A method according to claim 8 wherein collecting ECoG signals of user's brain activity comprises collecting ECoG signals having a significant frequency content (power) of more than about 40 Hz.

12. A method of controlling movement of a cursor on a computer monitor in real time comprising:
   monitoring electrocorticography (ECoG) signals of the brain activity of a subject;

analyzing the ECoG signals to determine the intent of the user with respect to the cursor movement;

comparing the intent of the user to a current position of the cursor;

generating from the intent of the user a device command to the computer monitor to move the cursor;

providing feedback to the user on the current position of the cursor;

reanalyzing the ECoG signal to determine an intended correction by the user with respect to the cursor movement;

communicating the intended correction by the user to the computer monitor to modify movement of the cursor.

13. The method in accordance with claim 12, wherein analyzing the ECoG signal comprises analyzing the ECoG to determine the intent of the user with respect to the cursor movement in at least two dimensions, and communicating the intent of the user to the display to move the cursor comprises moving the cursor in at least two dimensions.

* * * * *

UNITED STATES PATENT AND TRADEMARK OFFICE
CERTIFICATE OF CORRECTION

PATENT NO. : 7,120,486 B2
APPLICATION NO. : 10/735474
DATED : October 10, 2006
INVENTOR(S) : Eric C. Leuthardt et al.

It is certified that error appears in the above-identified patent and that said Letters Patent is hereby corrected as shown below:

ON THE FACE PAGE

Title Page

(73) Assignee: Washngton University, St. Louis, MO (US) should be

--Washington University, St. Louis, MO (US) and Health Research, Inc., Rensslaer, NY (US)--

Signed and Sealed this

Twenty-fifth Day of November, 2008

JON W. DUDAS
*Director of the United States Patent and Trademark Office*